(12) United States Patent
Khleif

(10) Patent No.: US 10,478,491 B2
(45) Date of Patent: Nov. 19, 2019

(54) METHODS FOR ENHANCING THE EFFICACY OF A TUMOR-DIRECTED IMMUNE RESPONSE

(71) Applicant: AUGUSTA UNIVERSITY RESEARCH INSTITUTE, INC., Augusta, GA (US)

(72) Inventor: Samir Khleif, Silver Spring, MD (US)

(73) Assignee: AUGUSTA UNIVERSITY RESEARCH INSTITUTE, INC., Augusta, GA (US)

(*) Notice: Subject to any disclaimer, the term of this patent is extended or adjusted under 35 U.S.C. 154(b) by 0 days.

(21) Appl. No.: 15/300,614

(22) PCT Filed: Apr. 2, 2015

(86) PCT No.: PCT/US2015/024034
§ 371 (c)(1),
(2) Date: Sep. 29, 2016

(87) PCT Pub. No.: WO2015/153857
PCT Pub. Date: Oct. 8, 2015

(65) Prior Publication Data
US 2017/0182156 A1    Jun. 29, 2017

Related U.S. Application Data

(60) Provisional application No. 61/974,781, filed on Apr. 3, 2014.

(51) Int. Cl.
*A61K 39/39* (2006.01)
*A61K 39/395* (2006.01)
*A61K 39/00* (2006.01)
*A61K 9/00* (2006.01)
*C07K 16/28* (2006.01)

(52) U.S. Cl.
CPC .......... *A61K 39/39* (2013.01); *A61K 9/0019* (2013.01); *A61K 39/0011* (2013.01); *C07K 16/2878* (2013.01); *A61K 2039/505* (2013.01); *A61K 2039/55511* (2013.01)

(58) Field of Classification Search
CPC .......................... A61K 39/395; A61K 39/0011
USPC ........................................................ 424/133.1
See application file for complete search history.

(56) References Cited

U.S. PATENT DOCUMENTS

| 6,312,700 | B1 | 11/2001 | Weinberg | |
|---|---|---|---|---|
| 7,504,101 | B2 | 3/2009 | Weinberg | |
| 7,622,444 | B2 | 11/2009 | Weinberg | |
| 7,959,925 | B2 | 6/2011 | Weinberg | |
| 8,580,844 | B2 | 11/2013 | Munn et al. | |
| 9,163,085 | B2 | 10/2015 | Liu et al. | |
| 2004/0253235 | A1* | 12/2004 | Durda | A61K 35/15 424/143.1 |
| 2009/0123467 | A1* | 5/2009 | Bedi | A61K 47/484 424/134.1 |
| 2013/0064831 | A1 | 3/2013 | Humphrey et al. | |
| 2013/0289083 | A1 | 10/2013 | Mautino et al. | |

FOREIGN PATENT DOCUMENTS

| WO | WO 95/12673 | 5/1995 | |
|---|---|---|---|
| WO | WO 95/21915 | 8/1995 | |
| WO | WO 2013119202 | * 8/2013 | ............... A61K 9/00 |
| WO | WO2013/130102 A2 | 9/2013 | |

OTHER PUBLICATIONS

Yang et al. (Experimental Biology and Medicine, 2010, 235: 869-876).*
Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
Gershoni, J., et al., "Epitope mapping—The first step in developing epitope-based vaccines", BIOD, ADIS International Ltd, NZ, 2007, vol. 21, No. 3, pp. 145-156.
Wainwright, D., et al., "Targeting Tregs in Malignant Brain Cancer: Overcoming IDO", Frontiers in Immunology, 2013, vol. 4, pp. 1-17.
Curti, B., et al., "OX40 is a Potent Immune-Stimulating Target in Late-Stage Cancer Patients", Cancer Research, 2013, vol. 73, No. 24, pp. 7189-7198.
Berrong, Z, et al., "Immune combinational therapy targeting OX40 and IDO synergistically enhances efficacy of a cancer vaccine", Journal for Immunotherapy of Cancer, Biomed Central LTD, London, UK, 2014, vol. 2, No. Suppl. 3, p. P226.
Supplementary European Search Report related to EP Application No. EP15773468 dated Sep. 12, 2017.
International Search Report related to PCT/US2015/024034 dated Jul. 8, 2015.
International Preliminary Report on Patentability and Written Opinion related to PCT/US2015/024034 dated Jul. 8, 2015.
Internet URL: www.cancer.gov/about-cancer/causes-prevention/risk/infectious-agents/hpv-fact-sheet; last accessed Dec. 13, 2018, pp. 1-6.
Weinberg et al., "Anti-OX40 (CD134) administration to nonhuman primates: immunostimulatory effects and toxicokinetic study." Journal of Immunotherapy, 29(6):575-85 (Nov. 2006).
Friedman et al., "Preparative immunotherapy with anti-OX40 and anti-CTLA4 improves the response to chemotherapy" Journal for ImmunoTherapy of Cancer 2(Supple 3):P207 (Nov. 2014).
Gough et al., "Targeting macrophages in the tumour environment to enhance the efficacy of αOX40 therapy." 136 (4):437-47 (Aug. 2012).

(Continued)

*Primary Examiner* — Yan Xiao
(74) *Attorney, Agent, or Firm* — McDonnell Boehnen Hulbert & Berghoff LLP

(57) ABSTRACT

As described below, the present invention features methods for enhancing the efficacy of a tumor antigen in inducing an anti-cancer immune response in a subject by administering an OX40 agonist and an Indoleamine 2,3-dioxygenase (IDO) inhibitor with the tumor antigen.

3 Claims, 15 Drawing Sheets

Specification includes a Sequence Listing.

(56) References Cited

OTHER PUBLICATIONS

Muller et al., "Inhibition of indoleamine 2,3-dioxygenase, an immunoregulatory target of the cancer suppression gene Bin1, potentiates cancer chemotherapy." Nat. Med. 11(3):312-9 (Mar. 2005).
Uyttenhove et al., "Evidence for a tumoral immune resistance mechanism based on tryptophan degradation by indoleamine 2,3-dioxygenase." Nat. Med. 9(10):1269-74 (Oct. 2003).
Yokouchi et al., "Anti-OX40 monoclonal antibody therapy in combination with radiotherapy results in therapeutic antitumor immunity to murine lung cancer." Cancer Sci. 99(2):361-7 (Feb. 2008).

\* cited by examiner

Figure 1A.

Therapeutic Study: Dose and schedule for anti-OX40 treatment alone or in a combination with vaccine

Antibody: Anti-OX40 (clone OX86)

Vaccine: CTL epitope from HPV16 E7 antigen, PADRE Thelper epitope and QuilA adjuvant.

Schedules: Anti-OX40 Ab treatment starting at Day 4 or Day 10 (1st day of tumor appearance) after tumor implantation

Doses: Twice a week 0.5, 1, and 2.5 mg/kg, i.p.

Readout: Survival

Number of groups: 14 groups (next slide) with n=5 mice/group

Experiment repeated twice – total of 140 C57/Bl6 mice were use (14 groups x 5 mice/group x 2 repeats)

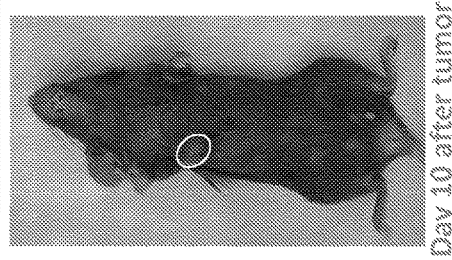

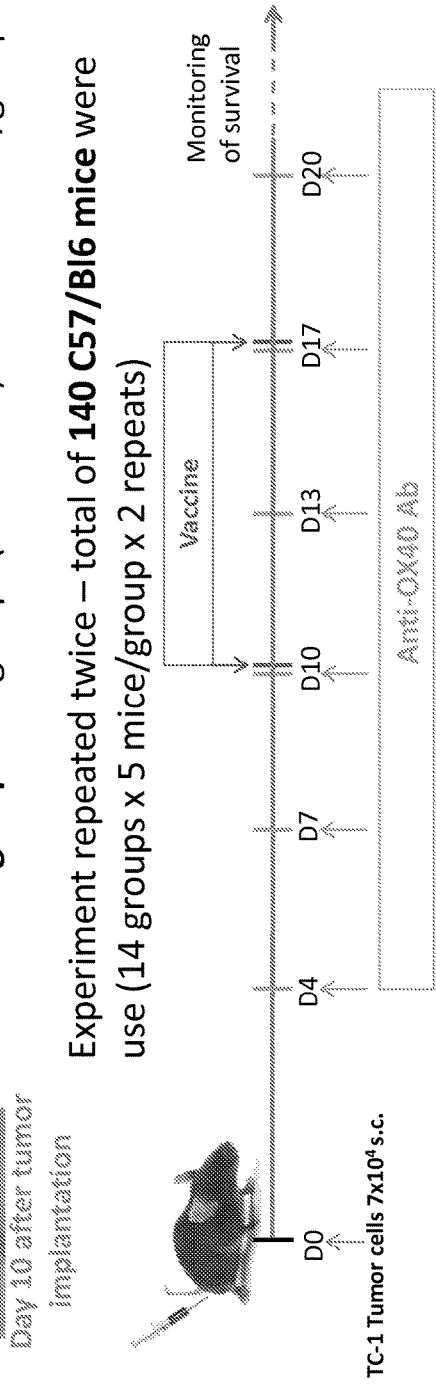

Therapeutic Study: Dose and schedule for anti-OX40 treatment alone or in a combination with vaccine

Figure 2A

Therapeutic Study: Dose and schedule for anti-OX40 treatment alone or in a combination with vaccine

Schedules: Anti-OX40 Ab treatment starting at Day 4 or Day 10 (1st day of tumor appearance) after tumor implantation
Doses: Twice a week 1, and 2.5 mg/kg, i.p.
Readout: Tumor growth
Number of groups: 6 groups with n=5 mice/group First study – total of 30 C57/Bl6 mice were used
Second study with another 30 C57/Bl6 mice (total of 60 mice)

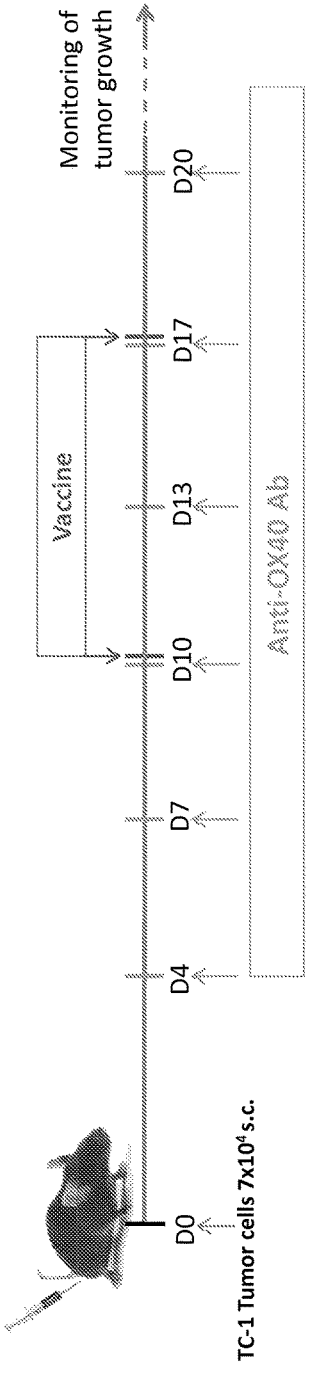

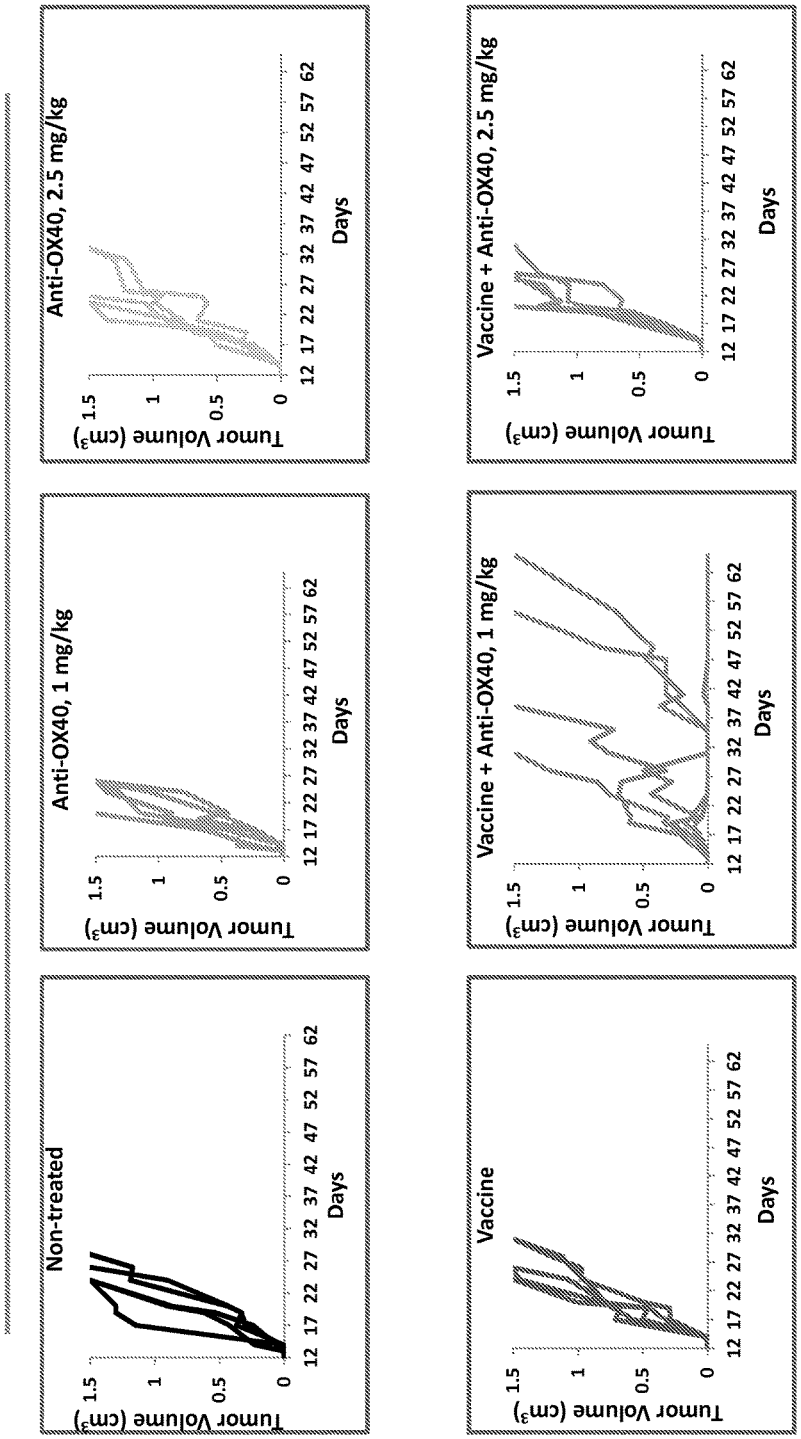

Immunology Study: Dose for anti-OX40 treatment alone or in a combination with vaccine

Doses: Twice a week 0.5, 1, and 2.5 mg/kg, i.p.
Readouts: Evaluation of antigen-specific immune response and tumor-infiltrating T cell profiles.
Number of groups: 8 groups with n=5 mice/group First study – total of 40 C57/Bl6 mice were used
Second study with another 40 C57/Bl6 mice (total of 80 mice)

Immunology Study: Dose for anti-OX40 treatment alone or in a combination with vaccine

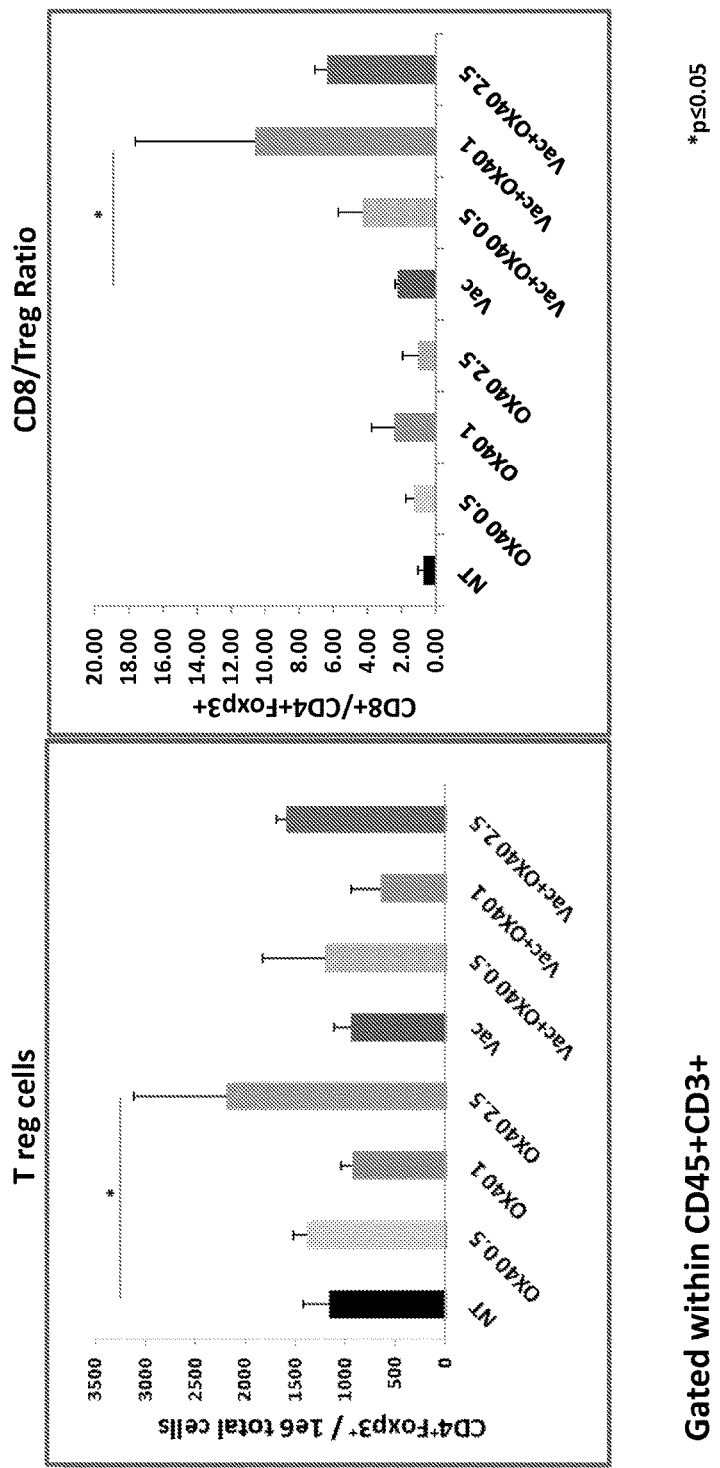

Figure 4A

Dissecting immune mechanisms for anti-OX40 Ab-based treatment

Schedule: Anti-OX40 Ab treatment starting on Day 10 (1st day of tumor appearance) after tumor implantation
Doses: Twice a week 1, 1.75, and 2.5 mg/kg, i.p.
Readout: Evaluation of splenic and tumor-infiltrating T cell profiles
Number of groups: 4 groups with n=5 mice/group First study – total of 20 C57/Bl6 mice were used
Second study with another 20 C57/Bl6 mice (total of 40 mice)

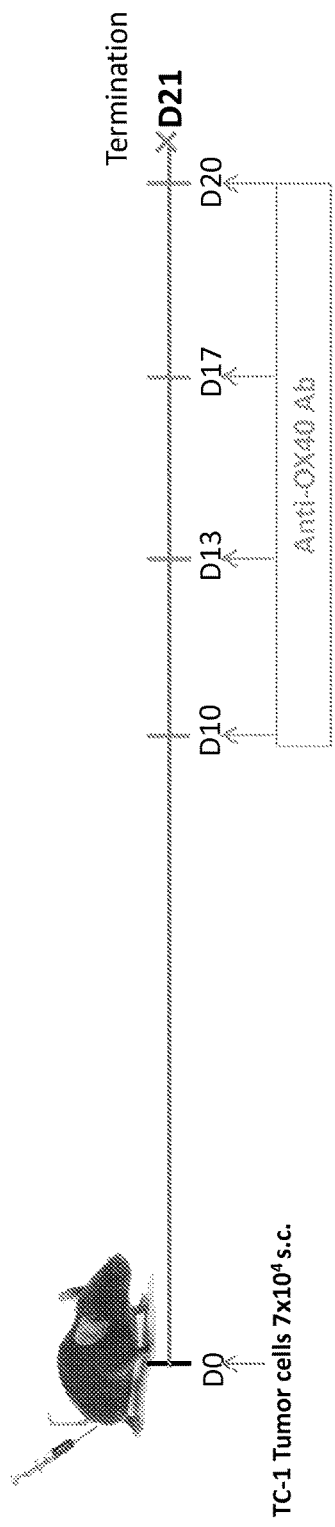

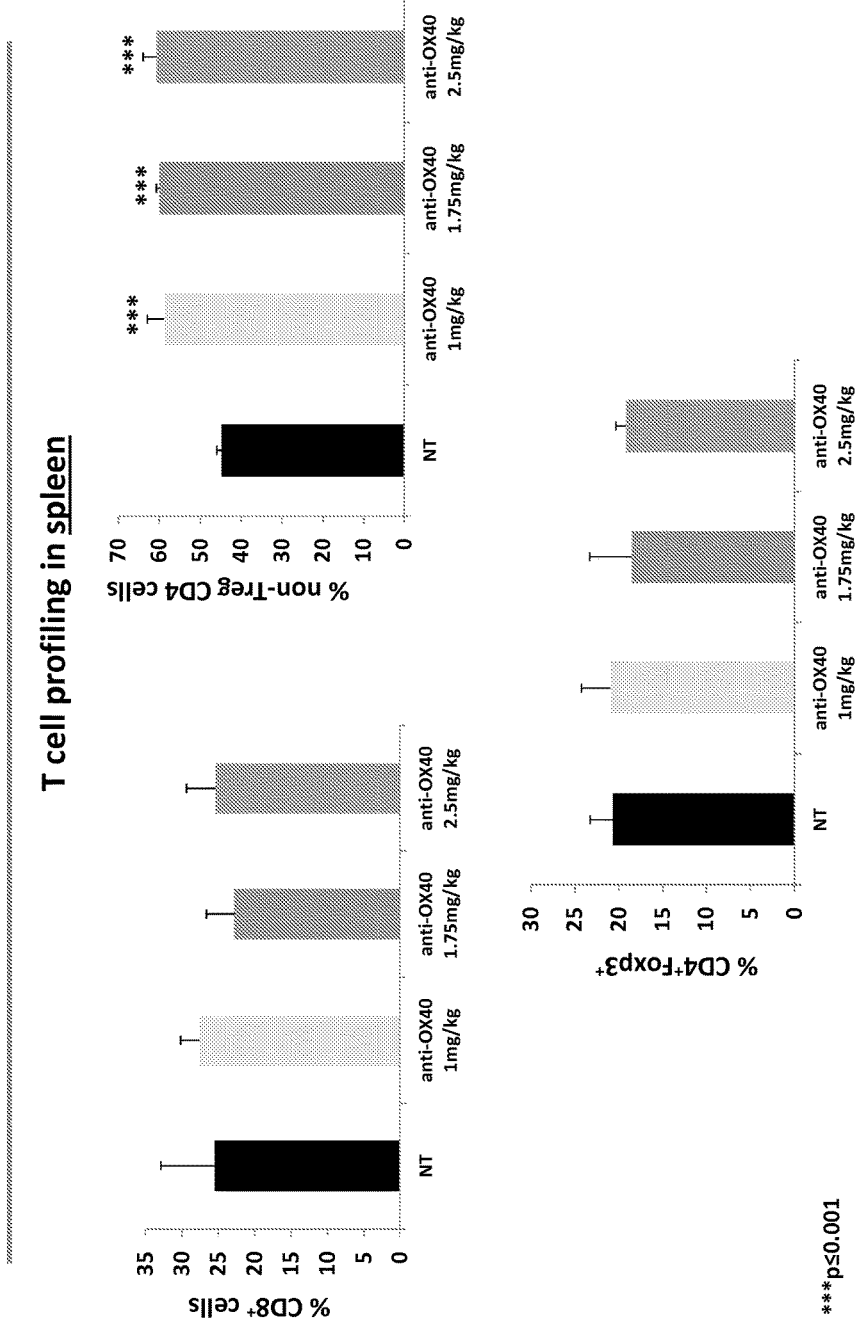

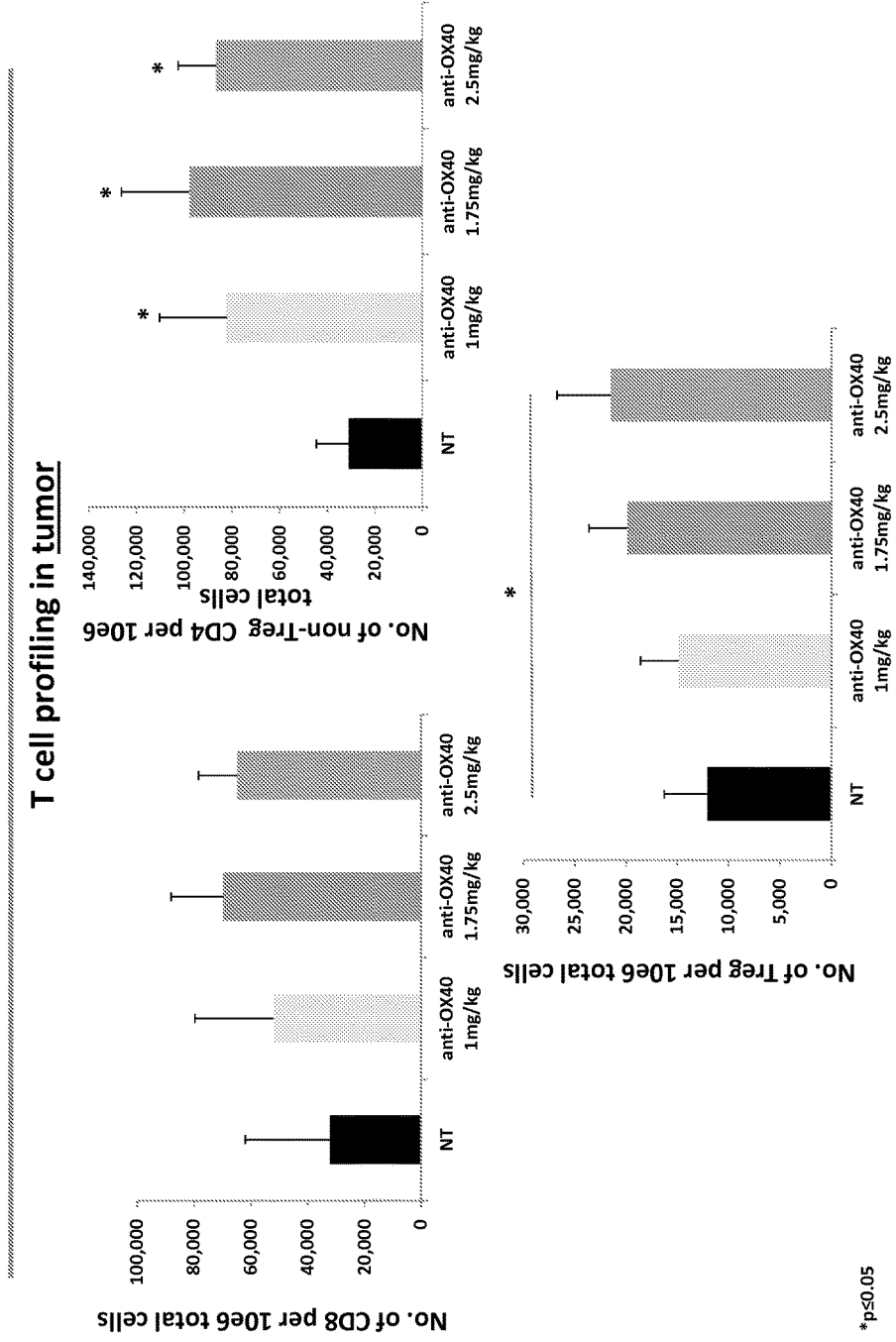

Figure 5A

Evaluation of the therapeutic efficacy of Vaccine/anti-OX40/1-MT combination treatment

Schedule: Anti-OX40 Ab treatment starting on Day 10 (1st day of tumor appearance) after tumor implantation. 1-MT is added to drinking water from day 10 till the end of experiment.
Doses: Anti-OX40 – 1mg/kg, 1-MT – 2mg/ml in drinking water.
Readout: Tumor growth and survival
Number of groups: 8 groups with n=5 mice/group First study – total of 40 C57/Bl6 mice were used
Second study with another 40 C57/Bl6 mice
Immunology study with same groups (40 C57/Bl6 mice) (total of 120 mice)

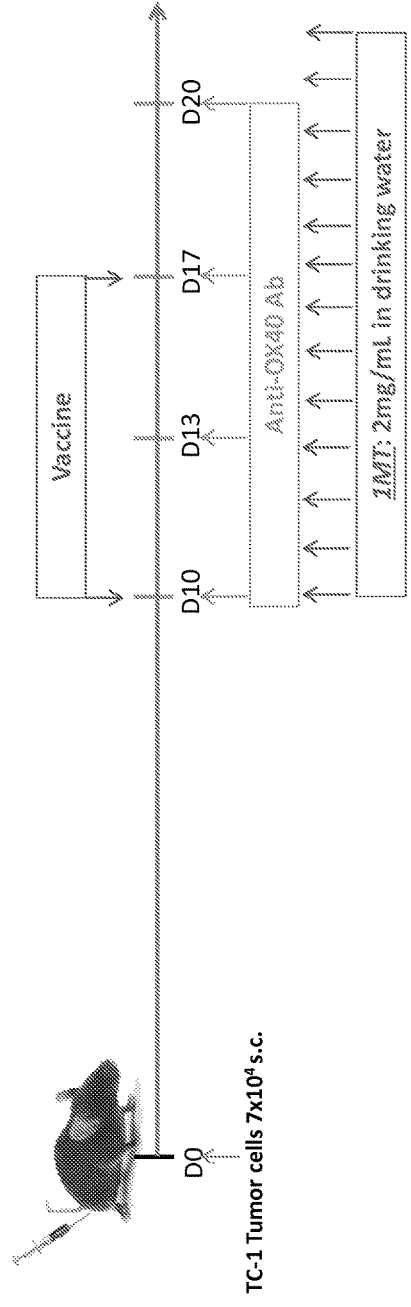

Evaluation of the therapeutic efficacy of Vaccine/anti-OX40/1-MT combination treatment

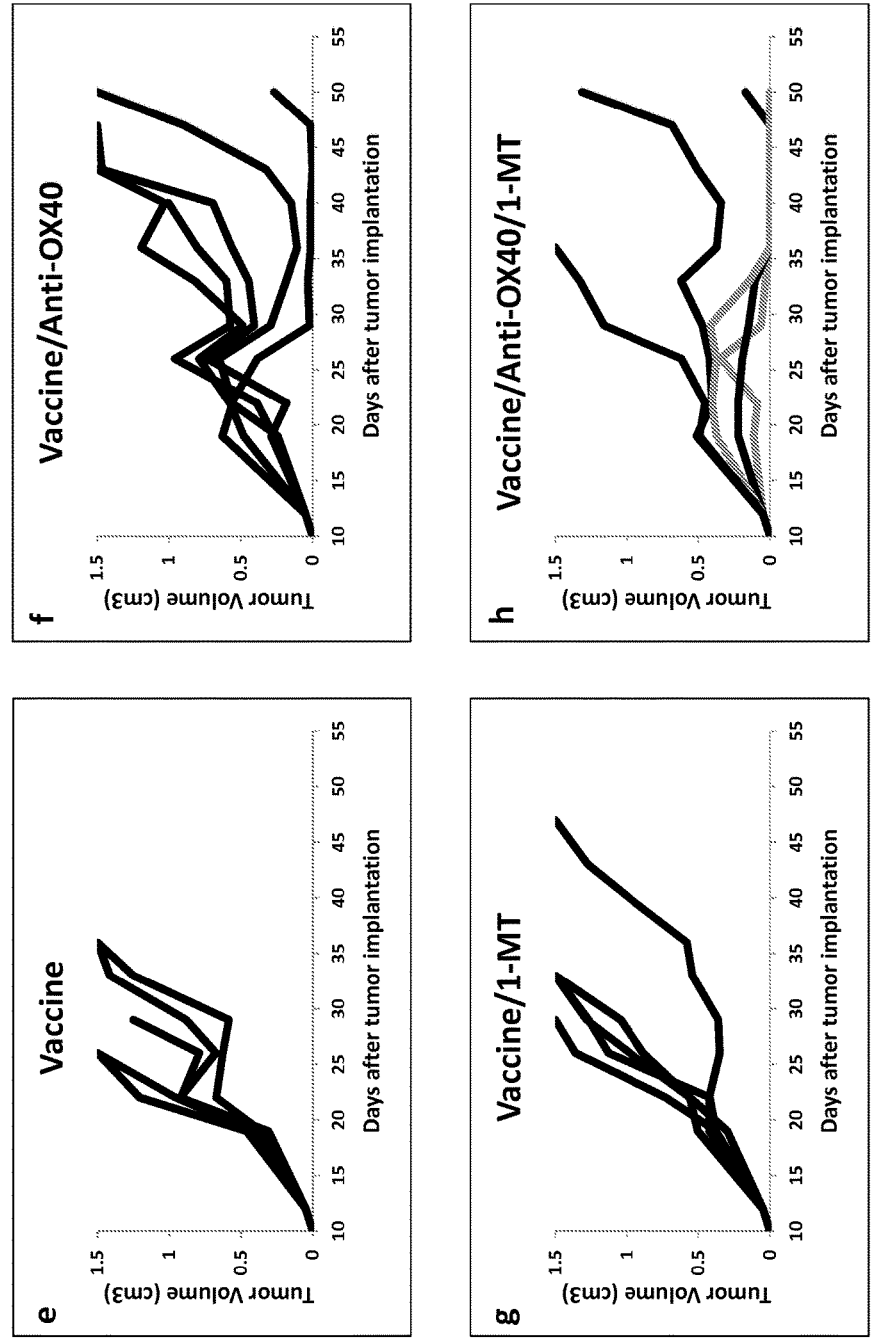

Evaluation of the therapeutic efficacy of Vaccine/anti-OX40/1-MT combination treatment Evaluation of the therapeutic efficacy of Vaccine/anti-OX40/1-MT combination treatment

METHODS FOR ENHANCING THE EFFICACY OF A TUMOR-DIRECTED IMMUNE RESPONSE

CROSS-REFERENCE TO RELATED APPLICATIONS

This application is a U.S. National Stage application of International Application No. PCT/US2015/024034, filed on Apr. 2, 2015, said International Application No. PCT/US2015/024034, claims benefit under 35 U.S.C. § 119(e) of the U.S. Provisional Application No. 61/974,781, filed Apr. 3, 2014. Each of the above listed applications is incorporated by reference herein in its entirety for all purposes.

REFERENCE TO THE SEQUENCE LISTING

This application incorporates by reference a Sequence Listing submitted with this application as text file entitled OX40-300_ST25.txt, created on Sep. 26, 2016, and having a size of 2,624 kilobytes.

BACKGROUND OF THE INVENTION

Patients with cancer typically exhibit adaptive immune responses against various tumor antigens. Despite the presence of this tumor-directed immune response, in many cases the patient's immune response is insufficient to block tumor growth and prolong survival. Cancer vaccines were originally designed to enhance the patient's own immune response. To date, the therapeutic potential of such cancer vaccines has not been realized. Accordingly, methods for enhancing the efficacy of a tumor-directed immune response are urgently required.

SUMMARY OF THE INVENTION

As described below, the present invention features methods for enhancing the efficacy of a tumor-directed immune response by administering an OX40 agonist and an Indoleamine 2,3-dioxygenase (IDO) inhibitor together with a tumor antigen. The tumor antigen may be present in a cancer vaccine or may be released from a tumor present in the subject, for example, by inducing apoptosis of a tumor cell. Apoptosis of tumor cells can be induced by any method known in the art (e.g., radiation, chemotherapy).

In one aspect, the invention features a method for enhancing an immune response against a tumor antigen in a subject, the method involving administering to the subject an OX40 agonist (e.g., an OX40 antibody agonist), an Indoleamine 2,3-dioxygenase (IDO) inhibitor (e.g., 1MT), and an immunogenic composition containing a tumor antigen (e.g., cancer vaccine), thereby enhancing the subject's immune response against the tumor antigen relative to administration of the immunogenic composition alone.

In another aspect, the invention features a method for delaying or reducing (e.g., by at least about 10%, 20%, 30%, 40%, 50%, 75%, 80%, 90% or 100%) tumor growth in a subject, the method involving administering to the subject an OX40 agonist, an Indoleamine 2,3-dioxygenase (IDO) inhibitor, and an immunogenic composition containing a tumor antigen, thereby delaying or reducing tumor growth in the subject relative to an untreated control subject.

In another aspect, the invention features a method for enhancing an immune response against a tumor antigen in a subject, the method involving administering to the subject radiation or a chemotherapeutic (e.g., anthracyclines (e.g., daunorubicin, doxorubicin, epirubicin, idarubicin, and valrubicin) or oxaliplatin) sufficient to induce tumor cell apoptosis, an OX40 agonist, and an Indoleamine 2,3-dioxygenase (IDO) inhibitor, thereby enhancing the subject's immune response against the tumor antigen relative to administration of the radiation or an anthracycline alone.

In another aspect, the invention features a method for delaying or reducing tumor growth in a subject, the method involving administering to the subject radiation or a chemotherapeutic (e.g., anthracyclines (e.g., daunorubicin, doxorubicin, epirubicin, idarubicin, and valrubicin) or oxaliplatin) sufficient to induce tumor cell apoptosis, an OX40 agonist, and an Indoleamine 2,3-dioxygenase (IDO) inhibitor, thereby delaying or reducing tumor growth in the subject relative to an untreated control subject.

In another aspect, the invention features a method for increasing the $CD8^+$ T cell to regulatory T cell ratio within a tumor in a subject, the method involving administering to the subject an effective amount of an OX40 agonist, an Indoleamine 2,3-dioxygenase (IDO) inhibitor, and an immunogenic composition containing a tumor antigen, thereby increasing the CD8/Treg ratio with the tumor.

In another aspect, the invention features a method for increasing the $CD8^+$ T cell to regulatory T cell ratio within a tumor in a subject, the method involving administering to the subject radiation or a chemotherapeutic (e.g., anthracyclines (e.g., daunorubicin, doxorubicin, epirubicin, idarubicin, and valrubicin) or oxaliplatin) sufficient to induce tumor cell apoptosis, an effective amount of an OX40 agonist, and an Indoleamine 2,3-dioxygenase (IDO) inhibitor, thereby increasing the CD8/Treg ratio with the tumor.

In another aspect, the invention features a method for enhancing an immune response against an HPV tumor antigen in a subject, the method involving administering to the subject an agonist OX40 antibody that binds the same OX40 epitope as mAb 9B12, 1-MT, and an immunogenic composition containing an HPV16 antigen and an adjuvant, thereby enhancing the subject's immune response against the tumor antigen relative to administration of the immunogenic composition alone.

In another aspect, the invention features a method for treating an HPV-related cancer in a subject, the method involving administering to the subject an agonist OX40 antibody that binds the same OX40 epitope as mAb 9B12, 1-MT, and an immunogenic composition containing an HPV16 antigen and an adjuvant, treating an HPV-related cancer in the subject.

In various embodiments of the above aspects or any other aspect of the invention delineated herein the method increases (e.g., by at least about 5%, 10%, 20%, 30% or more) the ratio of $CD8^+$ T cells to regulatory T cells within a tumor of the subject. In other embodiments of the above aspects, the amount of OX40 agonist administered is sufficient to increase the $CD8^+$ T cell to regulatory T cell ratio within a tumor of the subject. In still other embodiments of the above aspects, the amount of OX40 agonist administered is sufficiently low so as not to increase tumor-infiltrating Treg cells in the subject. In still other embodiments of the above aspects, the administration increases (e.g., by at least about 10%, 25%, 50%, 75%, or 100%) the subject's anti-tumor immune response relative to the administration of the immunogenic composition alone. In other embodiments of the above aspects, the Indoleamine 2,3-dioxygenase (IDO) inhibitor is 1-methyltryptophan (1-MT), the D isomer of 1-methyl-tryptophan, or NLG919. In other embodiments of the above aspects, the OX40 agonist specifically binds OX40. In other embodiments of the above aspects, the OX40 agonist is an antibody that specifically binds OX40 or an antigen-binding fragment thereof. In other embodiments of the above aspects, the antibody or antigen binding fragment thereof is a monoclonal antibody, a chimeric antibody, or a humanized antibody. In other embodiments of the above aspects, the antibody or antigen-binding fragment thereof binds to the same OX40 epitope as mAb 9B12. In other embodiments of the above aspects, the tumor antigen is any one or more of alpha fetoprotein, carcinoembryonic antigen, cdk4, beta-catenin, CA125, caspase-8, epithelial tumor antigen, an HPV antigen, HPV16 antigen, CTL epitope from HPV16 E7 antigen, melanoma associated antigen (MAGE)-1, MAGE-3, tyrosinase, surface Ig idiotype, Her-2/neu, MUC-1, prostate specific antigen (PSA), sialyl Tn (STn), heat shock proteins, gp96, ganglioside molecules GM2, GD2, GD3, carcinoembryonic antigen (CEA) and MART-1. In other embodiments of the above aspects, the amount of tumor antigen present in the immunogenic composition is sufficient to induce an anti-cancer immune response in the subject. In other embodiments of the above aspects, the administration of the immunogenic composition stimulates T-lymphocyte activity in the subject. In other embodiments of the above aspects, the immunogenic composition further contains an adjuvant. In other embodiments of the above aspects, the subject has a cancer selected from the group consisting of HPV-associated cancer, cervical cancer, penile cancer, anal cancer, squamous cell carcinoma of the head and neck and cancer of the vulvar. In other embodiments of the above aspects, the method increases subject survival by at least 10%, 20% or 30% or more relative to a subject that received administration of the immunogenic composition only. In other embodiments of the above aspects, the method reduces tumor growth by at least about 20% relative to tumor growth in an untreated control subject or induces tumor regression. In other embodiments of the above aspects, the subject is a human patient. In other embodiments of the above aspects, the immunogenic composition is a cancer vaccine.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "OX40" is meant a member of the TNFR-superfamily of receptors that is expressed on the surface of antigen-activated mammalian $CD4^+$ and $CD8^+$ T lymphocytes and regulatory T lymphocytes. See, for example, Paterson, D. J., et al. *Mol Immunol* 24, 1281-1290 (1987); Mallett, S., et al. *EMBO J* 9, 1063-1068 (1990); and Calderhead, D. M., et al. *J Immunol* 151, 5261-5271 (1993)). The terms "OX40" and "OX40 receptor" are used interchangeably herein. OX40 is also referred to as CD134, TNFRSF4, ACT-4, and ACT35. OX40 receptor sequences are known in the art and are provided, for example, at GenBank Accession Numbers: AAB33944 or CAE11757.

An exemplary human OX40 sequence is provided below:

```
  1   mcvgarrlgr gpcaallllg lglstvtglh cvgdtypsnd rcchecrpgn gmvsrcsrsq
 61   ntvcrpcgpg fyndvvsskp ckpctwcnlr sgserkqlct atqdtvcrcr agtqpldsyk
121   pgvdcapcpp ghfspgdnqa ckpwtnctla gkhtlqpasn ssdaicedrd ppatqpqetq
181   gpparpitvg pteawprtsq gpstrpvevp ggravaailg lglvlgllgp laillalyll
241   rrdqrlppda hkppgggsfr tpiqeeqada hstlaki
```

By "OX40 ligand" is meant a protein that specifically interacts with the OX40 receptor. See, for example, Baum P. R., et al. *EMBO J.* 13:3992-4001(1994)). OX40 ligand is also referred to as CD252, CD143L, gp34 and TNFSF4. The term OX40L includes the entire OX40 ligand, soluble OX40 ligand, and fusion proteins comprising a functionally active portion of OX40 ligand covalently linked to a second moiety, e.g., a protein domain. Also included within the definition of OX40L are variants which vary in amino acid sequence from naturally occurring OX4L but which retain the ability to specifically bind to the OX40 receptor. Further included within the definition of OX40L are variants which enhance the biological activity of OX40.

By "Ox40 agonist" is meant is a molecule that specifically interacts with and increases or enhances the biological activity of the OX40 receptor. Desirably, the biological activity is increased by at least about 10%, 20%, 30%, 50%, 70%, 80%, 90%, 95%, or even 100%. In certain aspects, OX40 agonists as disclosed herein include OX40 binding polypeptides, such as anti-OX40 antibodies (e.g., OX40 agonist antibodies), OX40 ligands, or fragments or derivatives of these molecules.

By "OX40 antibody" is meant an antibody that specifically binds OX40. OX40 antibodies include monoclonal and polyclonal antibodies that are specific for OX40 and antigen-binding fragments thereof. In certain aspects, anti-OX40 antibodies as described herein are monoclonal antibodies (or antigen-binding fragments thereof), e.g., murine, humanized, or fully human monoclonal antibodies. In one particular embodiment, the OX40 antibody is an OX40 receptor agonist, such as the mouse anti-human OX40 monoclonal antibody (9B12) described by Weinberg, A. D., et al. *J Immunother* 29, 575-585 (2006). In other embodiments, the antibody which specifically binds to OX40, or an antigen-binding fragment thereof binds to the same OX40 epitope as mAb 9B12.

By "antibody" is meant an immunoglobulin molecule that recognizes and specifically binds a target. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations.

By "ameliorate" is meant decrease, suppress, attenuate, diminish, arrest, or stabilize the development or progression of a disease.

By "antigen binding fragment" is meant a portion of an intact antibody that binds antigen. In particular, the term antigen binding fragment refers to the antigenic determining variable regions of an intact antibody. The antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

By "cancer" is meant a disease or disorder characterized by excess proliferation or reduced apoptosis. Illustrative cancers for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

By "chimeric antibody" is meant an antibody where the amino acid sequence of the immunoglobulin molecule is derived from two or more species. Typically, the variable region of both light and heavy chains corresponds to the variable region of antibodies derived from one species of mammal (e.g., mouse, rat, rabbit, etc) with the desired specificity, affinity, and functional capability while the constant regions are homologous to the sequences in antibodies derived from another (usually human) to avoid eliciting an immune response in that species.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "effective amount" is meant the amount of an agent described herein (e.g., OX40 agonist) required to ameliorate the symptoms of a disease relative to an untreated patient. The effective amount of such an agent used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "humanized antibody" is meant an antibody derived from a non-human immunoglobulin that has been engineered to contain human sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, *Nature,* 321:522-525; Riechmann et al., 1988, *Nature,* 332: 323-327; Verhoeyen et al., 1988, *Science,* 239:1534-1536). In some instances, the Fv framework region (FW) residues of a human immunoglobulin are replaced with the corresponding residues in an antibody from a non-human species that has the desired specificity, affinity, and capability.

A humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FW regions are those of a human immunoglobulin consensus sequence. A humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include antibodies that comprise, consist essentially of, or consist of, variants (including derivatives). Standard techniques known to those of skill in the art can be used to introduce mutations in the nucleotide sequence encoding a human antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

By "immunogenic composition" is meant a composition comprising an antigen capable of inducing an immune response when administered to a subject. The antigen (including a tumor antigen) is typically provided in a pharmaceutically acceptable excipient. If desired, the immunogenic composition comprises an adjuvant. In particular embodiments, a tumor antigen is provided by inducing the apoptosis of a tumor in situ, thereby releasing tumor antigens capable of inducing an immune response against the tumor.

By "monoclonal antibody" is meant a homogeneous antibody involved in the highly specific recognition and binding of a single antigenic determinant or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

By "enhances" is meant a positive alteration of at least 10%, 25%, 50%, 75%, or 100%.

By "reference" is meant a standard or control condition.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, or feline.

A "variable region" of an antibody refers to the variable region of the antibody light chain or the variable region of the antibody heavy chain, either alone or in combination. The variable regions of the heavy and light chain each consist of four framework regions (FW) connected by three complementarity determining regions (CDRs) also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.* 273:927-948)). In addition, combinations of these two approaches are sometimes used in the art to determine CDRs.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

A subject is successfully "treated" if the subject shows one or more of the following: a reduction in the number of or complete absence of cancer cells; a reduction in the tumor size; stabilization, retardation or reversal of tumor growth, inhibition of tumor growth includes, for example, suppression, prevention, retardation, shrinkage, or reversal of metastases (e.g., of cancer cell infiltration into peripheral organs including, for example, the spread of cancer into soft tissue and bone; inhibition); relief of one or more symptoms associated with cancer; reduced morbidity and mortality; improvement in quality of life; or some combination of these effects.

Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival in the absence of treatment, or as compared to subjects receiving standard therapy. Those in need of treatment include those already with the condition or disorder as well as those prone to have the condition or disorder or those in which the condition or disorder is to be prevented.

The terms "T cell" and "T-lymphocyte" may be used interchangeably to refer to a population of lymphocytes carrying a T cell receptor complex on the cell surface. While T-lymphocytes typically function in cell-mediated immunity, they can be divided into a number of sub-populations based not only on their particular functions, but also on the differential expression of certain surface and intracellular antigens that can function as "markers" for particular T-lymphocyte sub-populations. In general, helper T-cells express the surface antigen CD4 and cytotoxic T-cells express CD8. Sub-populations within these groups, and overlapping between these groups can be identified by other cell surface markers including, but not limited to CD95, CD25, FoxP3, CD28, CCR7, CD127, CD38, HLA-DR, and Ki-67. Sub-populations of T-lymphocytes can be identified and/or isolated from a mixed population of blood cells through the use of labeled antibodies, e.g., through flow cytometry or fluorescence activated cell sorting, described in more detail in the examples below. For example helper T cells can be identified as expressing CD3 and CD4, but not FoxP3. Other overlapping and non-overlapping subpopulations of T-lymphocytes include memory T cells, immature T cells, mature T cells, regulatory T cells (Tregs), activated T cells, and natural killer T (NKT) cells.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A and 1B show that administration of a cancer vaccine in combination with an anti-OX40 agonist antibody increased survival of mice in a tumorigenic mouse model. FIG. 1A depicts the design of a study of the effect of a cancer vaccine (CTL epitope from HPV16 E7 antigen, PADRE Thelper epitope and QuilA adjuvant) and anti-OX40 by measuring survival of mice in a mouse model of tumorigenesis. FIG. 1B are graphs showing that administering cancer vaccine and anti-OX40 agonist antibody at 1 mg/kg enhanced survival of mice in a tumorigenic mouse model (top right panel), compared to administering cancer vaccine alone or anti-OX40 alone, or administering cancer vaccine and anti-OX40 at lower (0.5 mg/kg, top left panel) or higher (2.5 mg/kg, bottom panel) doses. Of the mice receiving cancer vaccine and anti-OX40 agonist antibody at 1 mg/kg, ~20% were alive at up to about 62 days after injection of TC-1 tumor cells.

FIGS. 2A and 2B show that administration of a cancer vaccine in combination with an anti-OX40 agonist antibody inhibited tumor growth in mice in a tumorigenic mouse model. FIG. 2A depicts the design of a study of the effect of a cancer vaccine (CTL epitope from HPV16 E7 antigen, PADRE Thelper epitope and QuilA adjuvant) and anti-OX40 by measuring tumor growth in mice in a mouse model of tumorigenesis. FIG. 2B are graphs showing that administering cancer vaccine and anti-OX40 agonist antibody at 1 mg/kg inhibited tumor growth in a tumorigenic mouse model (bottom, middle panel), compared to administering cancer vaccine alone (bottom, left panel) or anti-OX40 alone (1 mg/kg, top middle panel; 2.5 mg/kg, top right panel), or administering cancer vaccine and anti-OX40 at higher (2.5 mg/kg; bottom right panel) doses. Of the mice receiving cancer vaccine and anti-OX40 agonist antibody at 1 mg/kg, mice showed reduced tumor volume and/or delays in tumor growth compared to the other study groups.

FIGS. 3A-3C show that administration of a cancer vaccine in combination with an anti-OX40 agonist antibody stimulated an antigen-specific immune response in mice in a tumorigenic mouse model. FIG. 3A depicts the design of a study of the effect of a cancer vaccine (CTL epitope from HPV16 E7 antigen, PADRE Thelper epitope and QuilA adjuvant) and anti-OX40 by evaluating antigen-specific immune response and tumor-infiltrating T cell profiles in a mouse model of tumorigenesis. FIG. 3B are graphs showing that mice receiving the cancer vaccine and anti-OX40 agonist antibody showed increases in antigen (E7) specific CD8 T cells in a tumorigenic mouse model, compared to mice receiving cancer vaccine alone or anti-OX40 alone. Mice receiving cancer vaccine and anti-OX40 agonist antibody at 1 mg/kg showed the highest ratio of E7-specific CD8 T cells:total CD8 T cells compared to the other groups receiving the cancer vaccine and anti-OX40. FIG. 3C are graphs showing that mice receiving the cancer vaccine and anti-OX40 agonist antibody showed increases in antigen (E7) specific CD8 T cells in a tumorigenic mouse model, compared to mice receiving cancer vaccine alone or anti-OX40 alone. Mice receiving cancer vaccine and anti-OX40 agonist antibody at 1 mg/kg showed the highest ratio of E7-specific CD8 T cells:regulatory T cells (Treg) compared to the other groups receiving the cancer vaccine and anti-OX40 at lower (0.5 mg/kg) or higher (2.5 mg/kg) doses.

FIGS. 4A-4C show that administration of a cancer vaccine in combination with an anti-OX40 agonist antibody increased tumor infiltration by regulatory T cells (Treg) in a tumorigenic mouse model. FIG. 4A depicts the design of a study of the effect of anti-OX40 antibody based treatment by evaluating splenic and tumor-infiltrating T cell profiles in a mouse model of tumorigenesis. FIG. 4B are graphs showing that mice receiving anti-OX40 agonist antibody (1 mg/kg; 1.75 mg/kg; 2.5 mg/kg) showed a significant increase in non-Treg CD4 T cells (CD4$^+$ FoxP3$^-$) in spleen, compared to mice receiving no treatment. Mice receiving anti-OX40 agonist antibody (1 mg/kg; 1.75 mg/kg; 2.5 mg/kg) had similar levels of CD8$^+$ cells (top left panel) and Treg cells (CD4$^+$ Foxp3$^+$; bottom panel) in spleen, compared to mice receiving no treatment. FIG. 4C are graphs showing that mice receiving anti-OX40 showed increased levels of tumor infiltrating Treg cells with increasing dosage of anti-OX40 (bottom panel).

FIGS. 5A-5D show that administration of a cancer vaccine in combination with an anti-OX40 agonist antibody and an indoleamine 2,3-dioxygenase (IDO) inhibitor inhibited tumor growth and increased survival in a tumorigenic mouse model. FIG. 5A depicts the design of a study of the effect of a cancer vaccine (CTL epitope from HPV16 E7 antigen, PADRE Thelper epitope and QuilA adjuvant), anti-OX40, and 1-methyltryptophan (1-MT) by measuring tumor growth and survival of mice in a mouse model of tumorigenesis. FIG. 5B are graphs showing that mice receiving the cancer vaccine, anti-OX40 agonist antibody (1 mg/kg), and 1-MT significantly inhibited and/or delayed tumor growth in a tumorigenic mouse model (panel h), compared to other groups of mice, including mice receiving cancer vaccine and anti-OX40 (panel 0 or cancer vaccine and 1-MT (panel g). Of the mice receiving cancer vaccine, anti-OX40 agonist antibody, and 1-MT, two mice showed a complete reduction in tumor volume ~35 days after injection of TC-1 tumor cells. FIG. 5C is a graph showing increased survival of mice receiving the cancer vaccine, anti-OX40 agonist antibody (1 mg/kg), and 1-MT, compared to other groups of mice, including mice receiving cancer vaccine and anti-OX40 (blue) or cancer vaccine and 1-MT (green). Mice receiving cancer vaccine, anti-OX40 agonist antibody, and 1-MT showed reduced tumor volume and/or delays in tumor growth compared to the other study groups. Up to ~80% survival was observed in these mice at up to about 55 days after injection of TC-1 tumor cells. FIG. 5D are graphs showing that inhibition of tumor growth and survival of mice were correlated. The tumor volumes and days survival were plotted for individual mice in the study.

DETAILED DESCRIPTION OF THE INVENTION

Figure 1B:
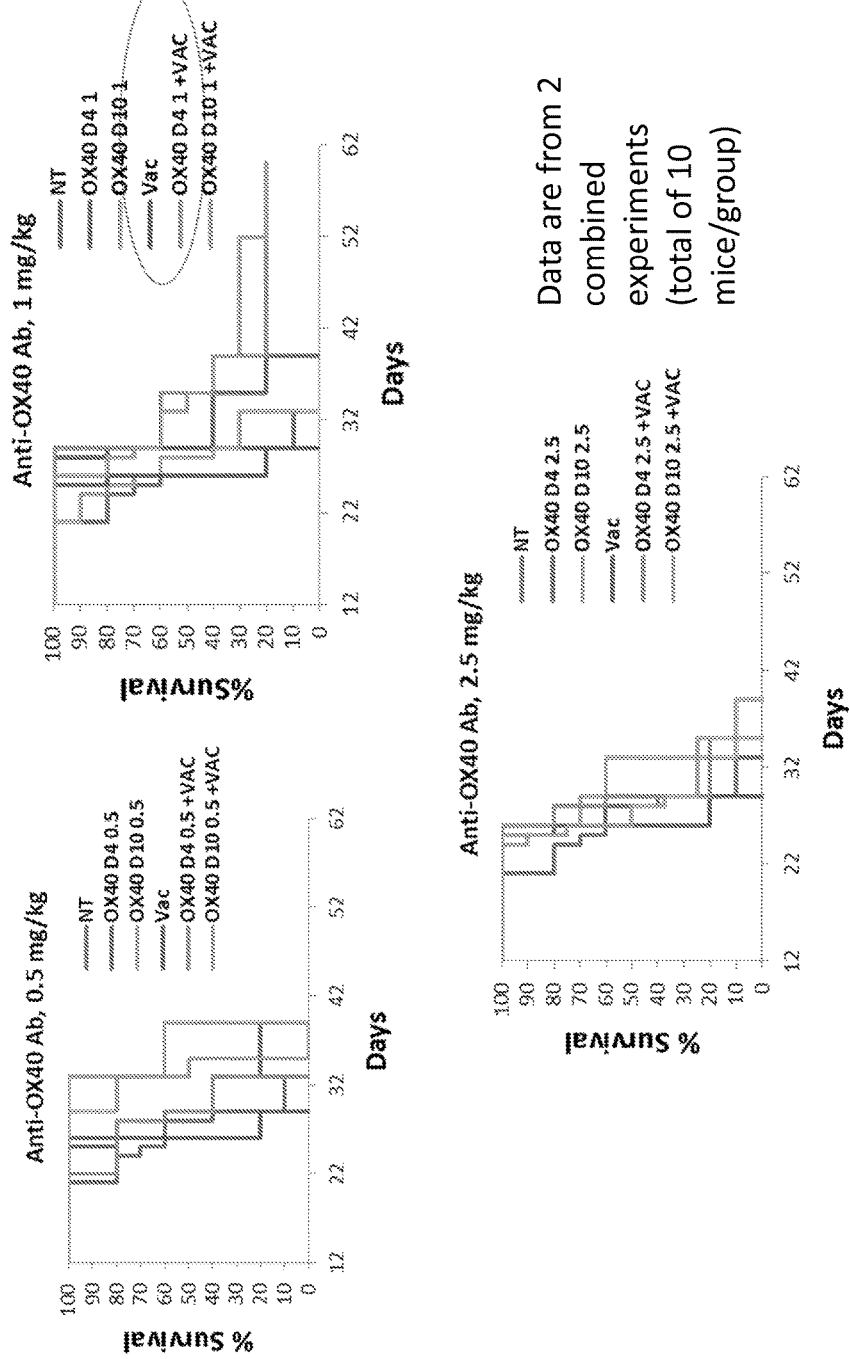

The invention features methods that are useful for enhancing the efficacy of a cancer vaccine.

The invention is based, at least in part, on the discovery that targeting the effector arm of the immune system with an agonist anti-OX40 antibody and the suppressor arm of the immune system with an IDO inhibitor enhanced the efficacy of a cancer vaccine. The OX40 molecule is a co-stimulatory receptor expressed on T cells that can lead to the proliferation and enhancement of T cell effector function when targeted with an agonist antibody. However, the effector T cells are suppressed by Indoleamine 2,3-dioxygenase (IDO) inhibitor, which is secreted by tumors as a protective mechanism against the tumor's destruction. As reported in detail below, treatment with anti-OX40 agonist antibody in combination with a cancer vaccine leads to the enhancement of antigen-specific T cell responses. The dose of 1 mg/kg anti-OX40 antibody stimulates the effector arm of T cells, which ultimately leads to a significant increase of $CD8^+$/regulatory T cell (Treg) ratio within tumors. Further, this combination of vaccine and anti-OX40 antibody treatment lead to a significant inhibition of tumor growth and prolonged mouse survival compared to untreated tumor (TC-1) bearing mice. A complete tumor regression was observed in 20% of treated mice. This effect was significantly enhanced, when the vaccine and anti-OX40 antibody treatment was combined with 1-MT, an indoleamine-(2,3)-dioxygenase (IDO) activity inhibitor. IDO has been shown to be secreted by tumor cells, suppressive dendritic cells and macrophages in tumor environment, and is known to be responsible for suppressing effector cells and inducing regulatory T cells. These data demonstrate that the combination of vaccine and anti-OX40 antibody with 1-methyltryptophan (1-MT, IDO inhibitor) lead to a more profound inhibition of tumor growth and complete regression of established tumors in 60% of mice. In conclusion, these findings indicate that simultaneous targeting of the effector arm of immunity with an anti-OX40 antibody and the suppressor arm of immunity with 1-MT, has a synergistic effect resulting in tumor eradication and is a promising strategy that can enhance the overall efficacy of cancer treatment in patients.

OX40

OX40 is a TNF-receptor family member that is expressed primarily on activated $CD4^+$ and $CD8^+$ T cells and regulatory T cells. OX40 agonists have potent anti-tumor activity against multiple tumor types, which is dependent on $CD4^+$ and $CD8^+$ T cells (Kjaergaard, J., et al. *Cancer Res* 60, 5514-5521 (2000); Weinberg, A. D., et al. *J Immunol* 164, 2160-2169 (2000); Gough, M. J., et al. *Cancer Res* 68, 5206-5215 (2008); Piconese, S., Valzasina, B. & Colombo, M. P. *J Exp Med* 205, 825-839 (2008)). OX40 agonists enhanced T cell proliferation, effector cytokine production, cytotoxicity, and decreased activation-induced cell death and increased the generation of memory T cells in non-human model systems (Gramaglia, I., et al. *J Immunol* 165, 3043-3050. (2000); Maxwell, J. R., et al. *J Immunol* 164, 107-112 (2000); Lee, S. W., et al. *J Immunol* 177, 4464-4472 (2006); Ruby, C. E. & Weinberg, A. D. *Cancer Immunol Immunother* 58, 1941-1947 (2009)).

OX40 Agonists

OX40 agonists interact with the OX40 receptor on $CD4^+$ T-cells during, or shortly after, priming by an antigen resulting in an increased response of the $CD4^+$ T-cells to the antigen. An OX40 agonist interacting with the OX40 receptor on antigen specific $CD4^+$ T-cells can increase T cell proliferation as compared to the response to antigen alone. The elevated response to the antigen can be maintained for a period of time substantially longer than in the absence of an OX40 agonist. Thus, stimulation via an OX40 agonist enhances the antigen specific immune response by boosting T-cell recognition of antigens, e.g., tumor cells. OX40 agonists are described, for example, in U.S. Pat. Nos. 6,312,700, 7,504,101, 7,622,444, and 7,959,925, which are incorporated herein by reference in their entireties. Methods of using such agonists in cancer treatment are described, for example, in WO/2013/119202 and in WO/2013/130102, each of which are incorporated herein by reference in its entirety.

OX40 agonists include, but are not limited to OX40 binding molecules, e.g., binding polypeptides, e.g., OX40 ligand ("OX40L") or an OX40-binding fragment, variant, or derivative thereof, such as soluble extracellular ligand domains and OX40L fusion proteins, and anti-OX40 antibodies (for example, monoclonal antibodies such as humanized monoclonal antibodies), or an antigen-binding fragment, variant or derivative thereof. Examples of anti-OX40 monoclonal antibodies are described, for example, in WO 95/12673 and WO/95/21915, the disclosures of which are incorporated herein by reference in their entireties. In certain embodiments, the anti-OX40 monoclonal antibody is 9B12, or an antigen-binding fragment, variant, or derivative thereof, as described in Weinberg, A. D., et al. *J Immunother* 29, 575-585 (2006), which is incorporated herein by reference in its entirety.

9B12 is a murine IgG1, anti-OX40 mAb directed against the extracellular domain of human OX40 (CD134) (Weinberg, A. D., et al. *J Immunother* 29, 575-585 (2006)). It was selected from a panel of anti-OX40 monoclonal antibodies because of its ability to elicit an agonist response for OX40 signaling, stability, and for its high level of production by the hybridoma. For use in clinical applications, 9B12 mAb is equilibrated with phosphate buffered saline, pH 7.0, and its concentration is adjusted to 5.0 mg/ml by diafiltration.

OX40 agonists include a fusion protein in which one or more domains of OX40L is covalently linked to one or more additional protein domains. Exemplary OX40L fusion proteins that can be used as OX40 agonists are described in U.S. Pat. No. 6,312,700, the disclosure of which is incorporated herein by reference in its entirety. In one embodiment, an OX40 agonist includes an OX40L fusion polypeptide that self-assembles into a multimeric (e.g., trimeric or hexameric) OX40L fusion protein. Such fusion proteins are described, e.g., in U.S. Pat. No. 7,959,925, which is incorporated by reference herein in its entirety. The multimeric OX40L fusion protein exhibits increased efficacy in enhancing antigen specific immune response in a subject, particularly a human subject, due to its ability to spontaneously assemble into highly stable trimers and hexamers.

In another embodiment, an OX40 agonist capable of assembling into a multimeric form includes a fusion polypeptide comprising in an N-terminal to C-terminal direction: an immunoglobulin domain, wherein the immunoglobulin domain includes an Fc domain, a trimerization domain, wherein the trimerization domain includes a coiled coil trimerization domain, and a receptor binding domain, wherein the receptor binding domain is an OX40 receptor binding domain, e.g., an OX40L or an OX40-binding fragment, variant, or derivative thereof, where the fusion polypeptide can self-assemble into a trimeric fusion protein. In one aspect, an OX40 agonist capable of assembling into a multimeric form is capable of binding to the OX40 receptor and stimulating at least one OX40 mediated activity. In certain aspects, the OX40 agonist includes an extracellular domain of OX40 ligand.

The trimerization domain of an OX40 agonist capable of assembling into a multimeric form serves to promote self-assembly of individual OX40L fusion polypeptide molecules into a trimeric protein. Thus, an OX40L fusion polypeptide with a trimerization domain self-assembles into a trimeric OX40L fusion protein. In one aspect, the trimerization domain is an isoleucine zipper domain or other coiled coli polypeptide structure. Exemplary coiled coil trimerization domains include: TRAF2 (GENBANK® Accession No. Q12933, amino acids 299-348; Thrombospondin 1 (Accession No. P07996, amino acids 291-314; Matrilin-4 (Accession No. O95460, amino acids 594-618; CMP (matrilin-1) (Accession No. NP-002370, amino acids 463-496; HSF1 (Accession No. AAX42211, amino acids 165-191; and Cubilin (Accession No. NP-001072, amino acids 104-138. In certain specific aspects, the trimerization domain includes a TRAF2 trimerization domain, a Matrilin-4 trimerization domain, or a combination thereof. In particular embodiments, an OX40 agonist is modified to increase its serum half-life. For example, the serum half-life of an OX40 agonist can be increased by conjugation to a heterologous molecule such as serum albumin, an antibody Fc region, or PEG. In addition, in certain embodiments mutations such as deletion, addition, or substitution mutations may be made to the antibodies or functional parts to improve their half-life. In one embodiment, the Fc region may be mutated to include one, two, or all three of the following substitutions M252Y, S254T, and T256E, wherein the numbering corresponds to the EU index in Kabat. In one embodiment, the Fc region may be mutated to include all of the following substitutions M252Y, S254T, and T256E, wherein the numbering corresponds to the EU index in Kabat. Dall'Acqua et al., Properties of Human IgG1s Engineered for Enhanced Binding to the Neonatal Fc Receptor (FcRn), J Biol Chem 281(33):23514-23524 (2006). The embodiment with all three substitutions is denoted as the YTE variant. Expressed differently, in one embodiment, the antibody or functional part has an Fc region having Y at position 252Y, T at position 254T, and E at position 256, wherein the numbering corresponds to the EU index in Kabat.

In certain embodiments, OX40 agonists can be conjugated to other therapeutic agents or toxins to form immunoconjugates and/or fusion proteins.

In certain aspects, an OX40 agonist can be formulated so as to facilitate administration and promote stability of the active agent. In certain aspects, pharmaceutical compositions in accordance with the present disclosure comprise a pharmaceutically acceptable, non-toxic, sterile carrier such as physiological saline, non-toxic buffers, preservatives and the like. Suitable formulations for use in the treatment methods disclosed herein are described, e.g., in Remington's Pharmaceutical Sciences (Mack Publishing Co.) 16th ed. (1980).

Desirably, administration of an OX40 agonist results in an enhanced T-lymphocyte response to antigens on a variety of cancer cells, because the activation of OX40, while functioning in concert with antigenic stimulation of T-lymphocytes, is not antigen or cell-specific itself. Thus, administration of the OX40 agonist can be used to enhance an immune response against virtually any tumor antigen.

An effective amount of an OX40 agonist to be administered can be determined by a person of ordinary skill in the art by well-known methods.

Clinical response to administration of an OX40 agonist can be assessed using diagnostic techniques known to clinicians, including but not limited to magnetic resonance imaging (MRI) scan, x-radiographic imaging, computed tomography (CT) scan, flow cytometry or fluorescence-activated cell sorter (FACS) analysis, histology, gross pathology, and blood chemistry, including but not limited to changes detectable by ELISA, RIA, and chromatography. In addition, the subject undergoing therapy with an OX40 agonist may experience the beneficial effect of an improvement in the symptoms associated with the disease.

Administration of the OX40 agonist can be via any usable route, as determined by the nature of the formulation and the needs of the patient. In certain embodiments, the OX40 agonist is administered by IV infusion.

Given that immune stimulation with OX40 agonists is not antigen-specific, a variety of cancers can be treated by the methods provided herein, for example in certain aspects, the cancer is a solid tumor, or a metastasis thereof. Types of cancers include, but are not limited to melanoma, gastrointestinal cancer, renal cell carcinoma, prostate cancer, lung cancer, or any combination thereof. The site of metastasis is not limiting and can include, for example metastases in the lymph node, lung, liver, bone, or any combination thereof.

The cancer treatment methods provided herein include conventional or non-conventional cancer treatments in addition to the administration of a cancer vaccine, an OX40 agonist, and the IDO inhibitor. By non-limiting example, administration of a cancer vaccine, an OX40 agonist, and the IDO inhibitor can be combined with surgery, radiation, chemotherapy, immunotherapy, targeting anti-cancer therapy, hormone therapy, or any combination thereof.

Effective treatment with an OX40 agonist includes, for example, reducing the rate of progression of the cancer, retardation or stabilization of tumor or metastatic growth, tumor shrinkage, and/or tumor regression, either at the site of a primary tumor, or in one or more metastases.

As reported herein below, administration of the OX40 agonist and the IDO inhibitor unexpectedly enhances the efficacy of the immunogenic composition comprising a tumor antigen.

Indoleamine 2,3-Dioxygenase Inhibitor

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, IFN-γ stimulation induces activation of IDO, which leads to a depletion of Trp, thereby arresting the growth of Trp-dependent intracellular pathogens, such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process.

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL-2) was believed to result from IDO released by the tumor cells in response to IFN-γ secretion by the PBLs. This effect was reversed by treatment with 1-methyl-tryptophan (1-MT), a specific IDO inhibitor. It was proposed that IDO activity in tumor cells may serve to impair anti-tumor responses (Logan, et al., 2002, Immunology, 105: 478-87).

Small molecule inhibitors of IDO useful in the methods of the invention are described, for example, in PCT Publication WO 99/29310, which reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities. IDO inhibitors, including Indoximod, the D isomer of 1-methyl-tryptophan, and NLG919, are known in the art and are commercially available, for example, from NewLink Genetics (Ames, Iowa). Other IDO inhibitors are described, for example, in US Patent Publication Nos. 20130289083, which is incorporated herein by reference in its entirety.

Generating an Anti-Cancer Immune Response

Cancer vaccines are potentially useful as therapeutics for the treatment of specific types of cancers. Advantageously, these vaccines may be tailored to treat the cancers of particular individuals, by generating immunogenic compositions that target specific tumor antigens expressed on a tumor in a subject. Cancer vaccines typically contain inactivated tumor cells or tumor antigens that stimulate a patient's immune system. The immune system responds to this stimulation by generating immunoresponsive cells that target the cancer. Unlike vaccines for other disease that prevent the occurrence of the disease, cancer vaccines are typically administered after a subject has been identified as having a neoplasia.

Antigen vaccines use tumor-specific antigens—proteins displayed on a tumor cell—to stimulate the immune system. By injecting these antigens into the cancerous area of the patient, the immune system produces antibodies or cytotoxic T lymphocytes to attack cancer cells that carry that specific antigen. Multiple antigens can be used in this type of vaccine to vary the immune system response.

Suitably, the tumor antigen is a tumor specific antigen (TSA) or a tumor associated antigen (TAA). Several tumor antigens and their expression patterns are known in the art and can be selected based on the tumor type to be treated. Non-limiting examples of tumor antigens include alpha fetoprotein (hepatocellular carcinoma), carcinoembryonic antigen (bowel cancer), cdk4 (melanoma), beta-catenin (melanoma), BING-4, CA125 (ovarian cancer), calcium-activated chloride channel 2, carcinoembryonic antigen, caspase-8 (squamous cell carcinoma), CDK4, CML66, cyclin-B1, Ep-Cam, epithelial tumor antigen (breast cancer), EphA3, fibronectin, an HPV antigen, HPV16 antigen, HPV 36, 37, CTL epitope from HPV16 E7 antigen, ART-2, melanoma associated antigen (MAGE)-1 and MAGE-3 (melanoma, breast, glioma), mesothelin, SAP-1, surviving, telomerase, tyrosinase (melanoma), surface Ig idiotype (e.g., BCR) (lymphoma), Her-2/neu (breast, ovarian), MUC-1 (breast, pancreatic), TAG-72, tyrosinase (melanoma), and HPV E6 and E7 (cervical carcinoma). Additional suitable tumor antigens include prostate specific antigen (PSA), RAS, sialyl Tn (STn), heat shock proteins and associated tumor peptides (e.g., gp96), ganglioside molecules (e.g., GM2, GD2, and GD3), carcinoembryonic antigen (CEA) and MART-1.

Typically immunogenic compositions comprising a tumor antigen are prepared in an injectable form, either as a liquid solution or as a suspension. Solid forms suitable for injection may also be prepared as emulsions, or with the polypeptides encapsulated in liposomes. The tumor antigen(s) are injected in any suitable carrier known in the art. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

Adjuvants are immunostimulating agents that enhance vaccine effectiveness. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Immunogenic compositions (e.g., cancer vaccines) are administered in a manner compatible with the dose formulation. By an effective amount is meant a single dose, or a vaccine administered in a multiple dose schedule, that is effective for the treatment or prevention of a disease or disorder. Preferably, the dose is effective to inhibit the growth of a neoplasm. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgment of the practitioner.

As reported herein below, administration of the IDO inhibitor (e.g., 1-MT) and the OX40 agonist (e.g., OX40 antibody agonist) synergistically enhances the efficacy of the cancer vaccine. Preferably, administration of the immunogenic composition comprising a tumor antigen, the OX40 antibody agonist, and the IDO inhibitor reduces or delays tumor growth, induces tumor regression, or increases patient survival relative to administration of such agents alone.

In addition to the use of cancer vaccines, therapies that induce tumor cell apoptosis release tumor antigens into the body that are capable of inducing an anti-cancer immune response. In one embodiment, radiation may be used to induce tumor cell apoptosis. Accordingly, the invention provides methods for enhancing the efficacy of a tumor antigen in inducing an anti-cancer immune response by administering an OX40 agonist and an Indoleamine 2,3-dioxygenase (IDO) inhibitor in combination with radiation therapy. In another embodiment, chemotherapy that induces tumor cell apoptosis (e.g., anthracyclines, oxaliplatin) can be administered in combination with an OX40 agonist and an Indoleamine 2,3-dioxygenase (IDO) inhibitor. Exemplary anthracyclines include, but are not limited to, daunorubicin, doxorubicin, epirubicin, idarubicin, and valrubicin.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Treatment with a Cancer Vaccine and an Anti-OX40 Agonist Antibody Increased Survival in a Tumorigenic Mouse Model A study was performed in a tumorigenic mouse model to determine the effect of treatment with a cancer vaccine (CTL epitope from HPV16 E7 antigen, PADRE T-helper epitope and QuilA adjuvant) and OX40 agonist on survival (FIG. 1A). Mice (C57BL6; female, 6-8 weeks old) were injected with TC-1 tumor cells ($7 \times 10^4$ s.c.). Administration of anti-OX40 antibody (clone OX86) was started at day 4 or day 10 after injection with TC-1 cells. The first day of tumor appearance was around day 10. Anti-OX40 antibody was administered twice a week at 0.5, 1.0, and 2.5 mg/kg doses, i.p. In all, 14 groups of mice (n=5/group) were studied, including mice receiving no treatment, vaccine alone, anti-OX40 alone at day 4 (0.5, 1.0, and 2.5 mg/kg), anti-OX40 alone at day 10 (0.5, 1.0, and 2.5 mg/kg), anti-OX40 at day 4 (0.5, 1.0, and 2.5 mg/kg) and cancer vaccine, and anti-OX40 at day 10 (0.5, 1.0, and 2.5 mg/kg) and cancer vaccine. The study was repeated twice.

Mice administered cancer vaccine and anti-OX40 agonist antibody at 1 mg/kg showed enhanced survival, compared to mice administered cancer vaccine alone or anti-OX40 alone (FIG. 1B). In particular, mice administered cancer vaccine and anti-OX40 at lower (0.5 mg/kg, top left panel) or higher (2.5 mg/kg, bottom panel) doses did not show enhanced survival. Of the mice receiving cancer vaccine and anti-OX40 agonist antibody at 1 mg/kg, ~20% were alive at up to about 62 days after injection of TC-1 tumor cells. No significant difference in survival was provided when anti-OX40 antibody was given prior to tumor appearance (day 4 after tumor implantation) or on the first day of tumor appearance (day 10 after tumor implantation).

Example 2. Treatment with a Cancer Vaccine and an Anti-OX40 Agonist Antibody Decreased Tumor Growth in a Tumorigenic Mouse Model A study was performed in a tumorigenic mouse model to determine the effect of treatment with a cancer vaccine (CTL epitope from HPV16 E7 antigen, PADRE Thelper epitope and QuilA adjuvant) and OX40 agonist on tumor growth (FIG. 2A). Mice (C57BL6; female, 6-8 weeks old) were injected with TC-1 tumor cells ($7 \times 10^4$ s.c.). Administration of anti-OX40 antibody (clone OX86) was started at day 4 or day 10 after injection with TC-1 cells. Anti-OX40 antibody was administered twice a week at 1.0, and 2.5 mg/kg doses, i.p. In all, 6 groups of mice (n=5/group) were studied, including mice receiving no treatment, vaccine alone, anti-OX40 alone (1.0, and 2.5 mg/kg), and anti-OX40 (1.0 and 2.5 mg/kg) and cancer vaccine. The study was repeated twice.

Mice administered cancer vaccine and anti-OX40 agonist antibody at 1 mg/kg showed reduced tumor volume and/or delays in tumor growth (FIG. 2B: bottom, middle panel), compared to mice administered cancer vaccine alone (FIG. 2B: bottom, left panel) or anti-OX40 alone (FIG. 2B: top middle panel, top right panel). Consistent with other results (see, e.g., FIG. 1B), mice administered cancer vaccine and anti-OX40 at a higher dose (2.5 mg/kg) did not show the same effect on tumor growth as mice receiving cancer vaccine and anti-Ox40 agonist antibody at 1 mg/kg (FIG. 2B: bottom right panel). Thus, treatment with a cancer vaccine and anti-OX40 agonist antibody at 1 mg/kg inhibited tumor growth in mice.

Figure 3A:
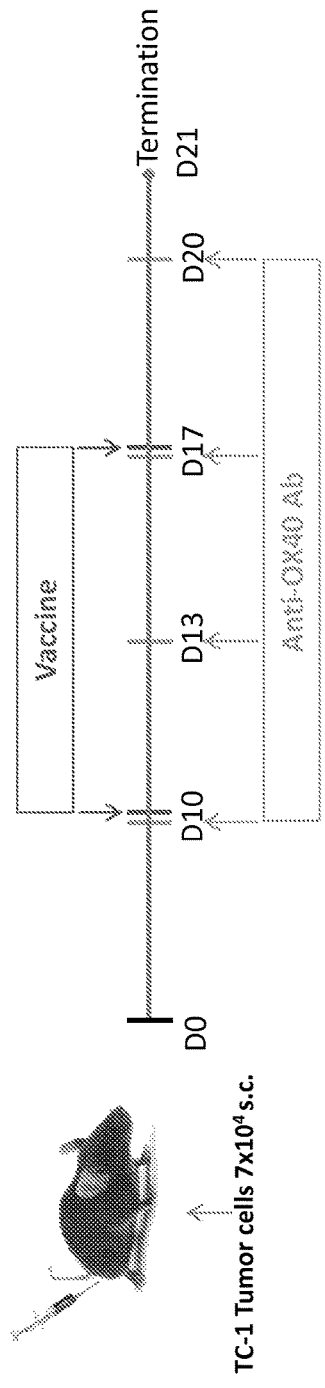
Figure 3B:
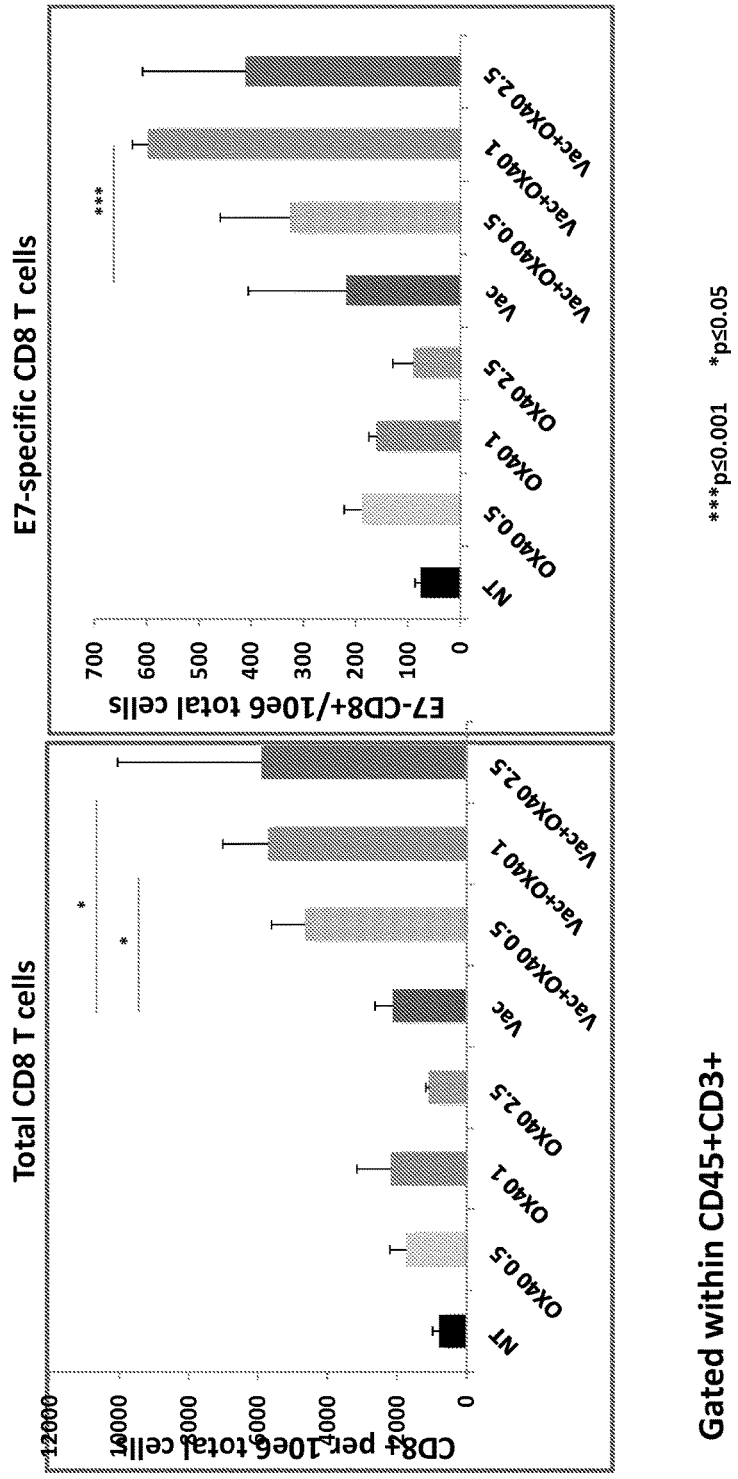

Example 3. Treatment with Cancer Vaccine and an Anti-OX40 Agonist Antibody Increased CD8/Treg Ratio within a Tumor in a Tumorigenic Mouse Model A study was performed in a tumorigenic mouse model to evaluate the effect of treatment with a cancer vaccine (CTL epitope from HPV16 E7 antigen, PADRE Thelper epitope and QuilA adjuvant) and OX40 agonist on immune response (FIG. 3A). Mice (C57BL6; female, 6-8 weeks old) were injected with TC-1 tumor cells ($7 \times 10^4$ s.c.). Administration of anti-OX40 antibody (clone OX86) was started at day 10 after injection with TC-1 cells. Anti-OX40 antibody was administered twice a week at 0.5, 1.0, or 2.5 mg/kg doses, i.p. In all, 8 groups of mice (n=5/group) were studied, including mice receiving no treatment, vaccine alone, anti-OX40 alone (0.5 and 1.0 mg/kg), and anti-OX40 (0.5, 1.0, and 2.5 mg/kg) and cancer vaccine. The study was repeated twice. FIGS. 3B and 3C show the effect of various doses of Ox40 alone, or in combination with vaccine on CD8 T cells, E7-specific CD8 T cells, T reg cells, and the CD8/Treg ratio.

Example 4. Treatment with Cancer Vaccine and an Anti-OX40 Agonist Antibody Stimulated an Antigen-Specific Immune Response in a Tumorigenic Mouse Model A study was performed in a tumorigenic mouse model to evaluate the effect of treatment with a cancer vaccine (CTL epitope from HPV16 E7 antigen, PADRE Thelper epitope and QuilA adjuvant) and OX40 agonist on immune response (FIG. 4A). Mice (C57BL6; female, 6-8 weeks old) were injected with TC-1 tumor cells ($7 \times 10^4$ s.c.). Administration of anti-OX40 antibody (clone OX86) was started at day 10 after injection with TC-1 cells. Anti-OX40 antibody was administered twice a week at 1.0, 1.75, or 2.5 mg/kg doses, i.p. In all, 4 groups of mice (n=5/group) were studied, including mice receiving no treatment and anti-OX40 alone (1.0, 1.75, and 2.5 mg/kg). The study was repeated twice.

No effect on percentage or number of CD8+ T-cells in spleen (FIG. 4B: top left panel) or tumor (FIG. 4C: top right panel) was detected after treatment with anti-OX40 antibody for all doses. All three doses significantly increased non-Treg CD4 T cells (CD4+ FoxP3−) in the spleen (FIG. 4B, top right panel) and within the tumor (FIG. 4C, top right panel). Mice receiving anti-OX40 agonist antibody had similar levels of Treg cells (CD4+ Foxp3+; FIG. 4B: bottom panel), compared to mice receiving no treatment. However, mice receiving anti-OX40 showed increased levels of tumor infiltrating Treg cells with increasing dosage of anti-OX40 (FIG. 4C: bottom panel). Without being bound to a particular theory, the increase in tumor infiltrating Treg cells might explain a lack of therapeutic effect when 2.5 mg/kg of anti-OX40 Ab was used with the cancer vaccine.

Example 5. Treatment with Cancer Vaccine, Anti-OX40 Agonist Antibody, and Indoleamine 2,3-Dioxygenase (IDO) Inhibitor Decreased Tumor Growth and Increased Survival in a Tumorigenic Mouse Model Mouse tumor TC-1, which expresses the E7 oncoprotein from HPV-16, is used as a surrogate for human tumors infected with HPV-16. Mice (C57BL6; female, 6-8 weeks old) were injected with TC-1 tumor cells (7×104 s.c.) at Day 0. Administration of anti-OX40 antibody (clone OX86) was started at day 10 after injection with TC-1 cells. The anti-OX40 antibody was administered twice a week at 1.0 mg/kg, i.p. Starting at day 10, 1-methyl-tryptophan (1-MT) was administered to the mice by adding 1-MT (2 mg/mL) to their drinking water. In all, 8 groups of mice (n=5/group) were studied, including mice receiving no treatment, anti-OX40 alone (1.0 mg/kg), 1-MT alone, anti-OX40 and 1-MT, cancer vaccine alone, cancer vaccine and anti-OX40 (1.0 mg/kg), cancer vaccine and 1-MT, and cancer vaccine, anti-OX40, and 1-MT.

Figure 5B:
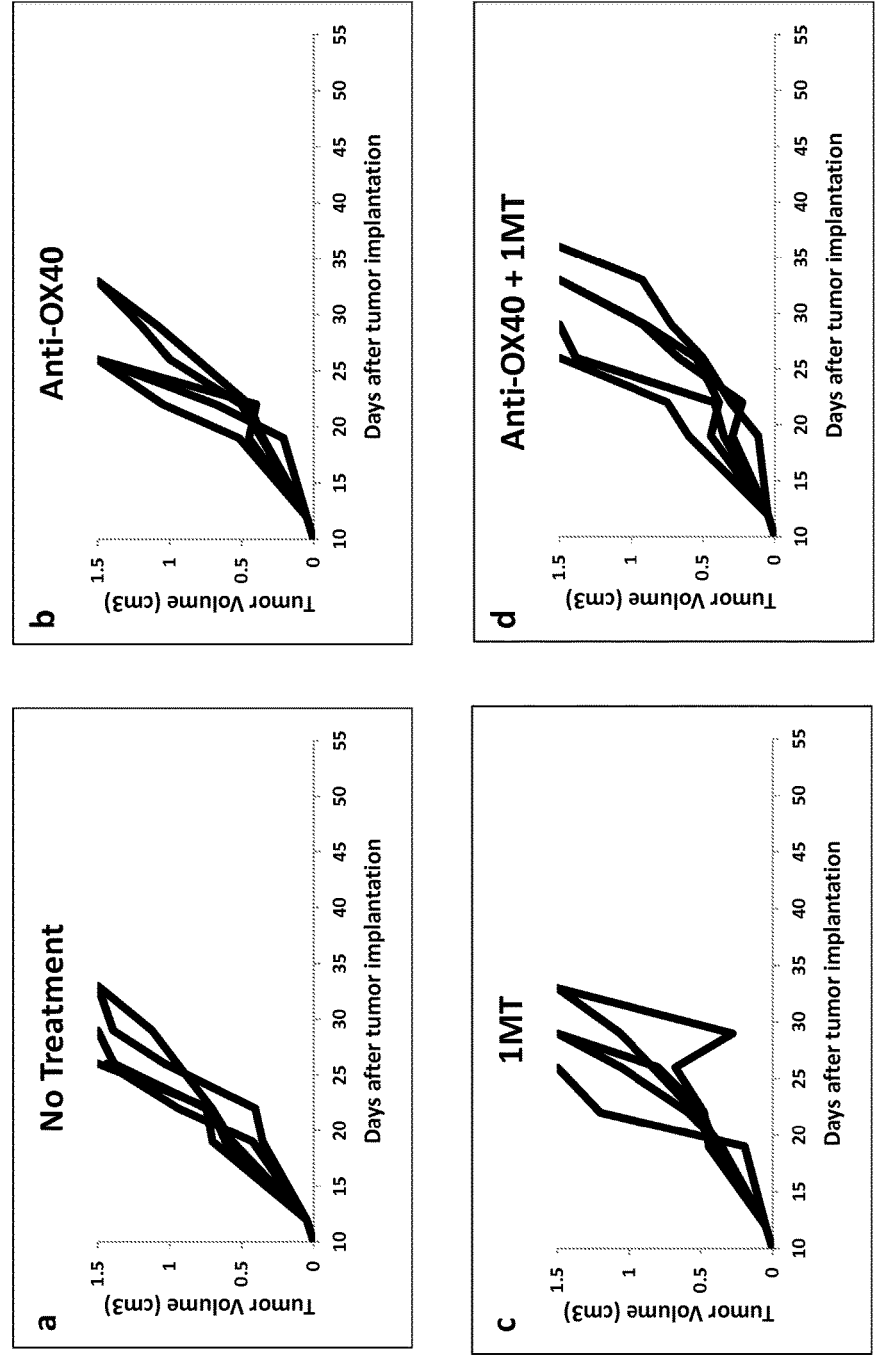
Figure 5C:
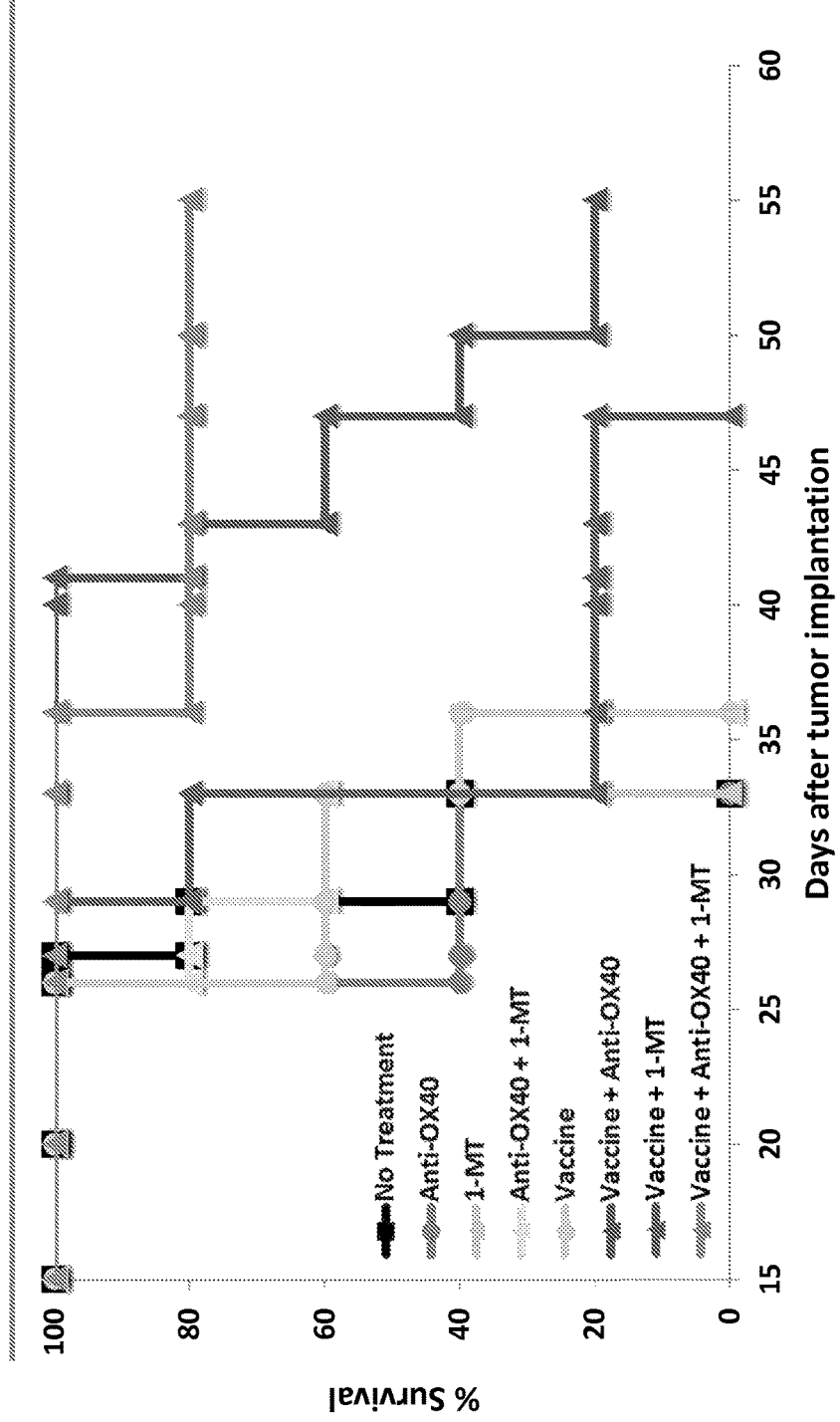
Figure 5D:
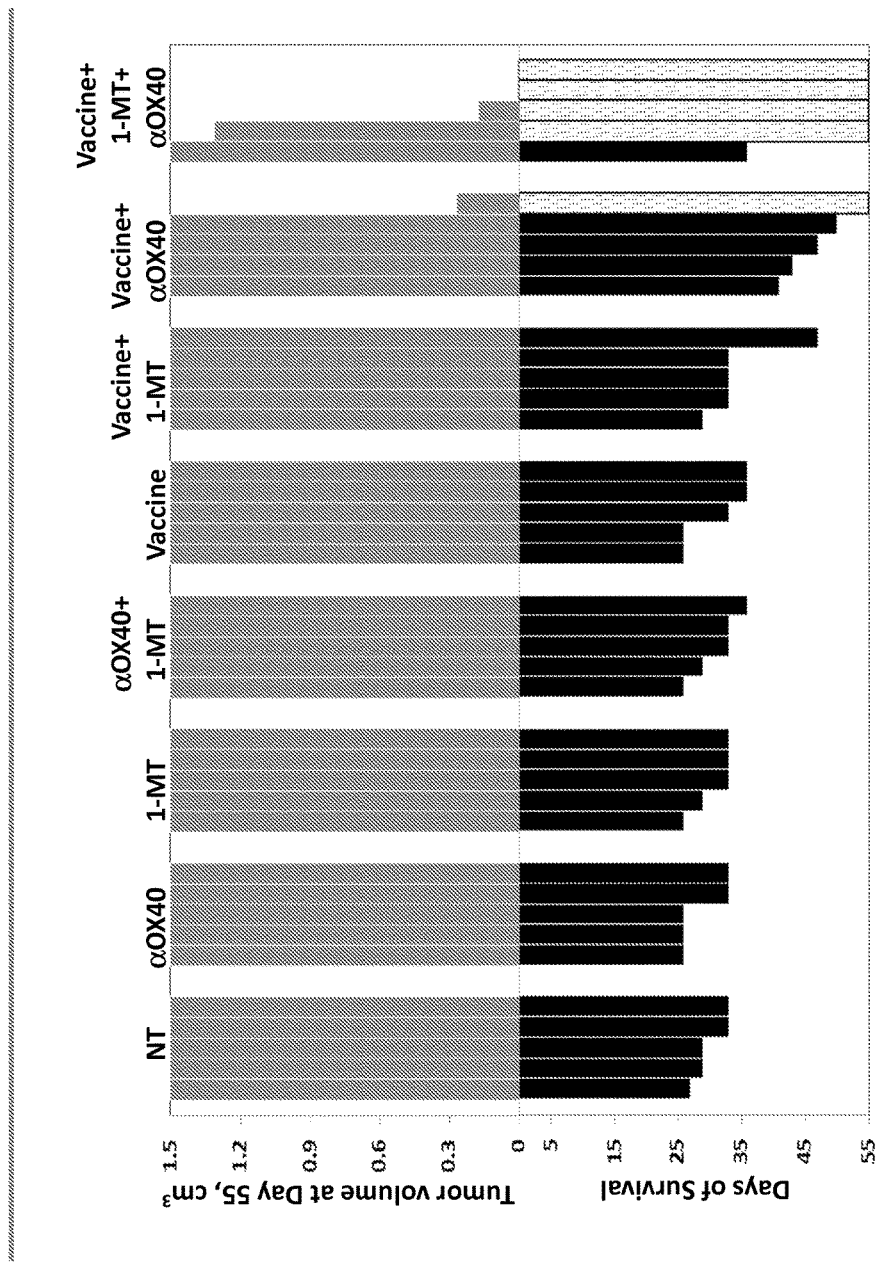

Mice receiving the cancer vaccine, anti-OX40 agonist antibody (1 mg/kg), and 1-MT significantly inhibited and/or delayed tumor growth in a tumorigenic mouse model (FIG. 5B: panel h), compared to other groups of mice, including mice receiving cancer vaccine and anti-OX40 (FIG. 5B: panel 0 or cancer vaccine and 1-MT (FIG. 5B: panel g). Of the mice receiving cancer vaccine, anti-OX40 agonist antibody, and 1-MT, two mice showed a complete reduction in tumor volume ~35 days after injection of TC-1 tumor cells. Mice receiving the cancer vaccine, anti-OX40 agonist antibody (1 mg/kg) (red), and MT-1 had increased survival compared to other groups of mice, including mice receiving cancer vaccine and anti-OX40 (blue) or cancer vaccine and 1-MT (green) (FIG. 5C). Up to ~80% survival was observed in these mice at up to about 55 days after injection of TC-1 tumor cells. In contrast, ~20% mice receiving cancer vaccine and anti-OX40 agonist antibody were alive up to about 55 days after injection of TC-1 tumor cells, consistent with previous results (see, e.g., FIG. 1B). The inhibition of tumor growth and survival of mice were correlated (FIG. 5D). Thus, the addition of 1-MT to treatment with cancer vaccine and anti-OX40 led to a significant increase in therapeutic potency of treatment (e.g., 60% vs. 20% complete regression). The results presented herein demonstrate that use of OX40 agonists and IDO inhibitors in combination with cancer vaccines has the potential to increase the efficacy of cancer vaccines.

The results described herein above were carried out using the following materials and methods.

Mice (C57BL6; female, 6-8 weeks old) were obtained from Jackson Laboratory (Bar Harbor, Me.) and kept under pathogen-free conditions.

TC-1 cells that were derived by co-transfection of human papilloma-virus strain 16 (HPV16) early proteins 6 and 7 (E6 and E7) and activated ras oncogene to primary C57BL/6 mouse lung epithelial cells were obtained from ATCC (Manassas, Va.). TC-1 cells were grown in RPMI 1640 supplemented with 10% FBS, penicillin and streptomycin (100 U/ml each) and L-glutamine (2 mM) at 37° C. with 5% $CO_2$.

Vaccine consisting of CTL epitope from E7 antigen ($E7_{49-57}$, a 9-mer peptide (RAHYNIVTF)), mixed with PADRE 13-mer T helper epitope (aKChaVAAWTLKAAa) (both from Celtek Bioscience (Nashville, Tenn.)) and QuilA adjuvant (Brenntag, Denmark). Anti-OX40 antibody (clone OX86) was provided by Medimmune. 1-Methyl-D-Tryptophan (1-MT) was obtained from Sigma-Aldrich (St. Louis, Mo.).

In the experiments where analysis of tumor growth and survival were the endpoint, mice (n=5/group) were implanted with 70,000 TC-1 cells on day 0. Anti-OX40 antibody (1 mg/kg, i.p.) was injected either on day 4 or day 10 after tumor implantation. On day 10, when all mice had tumors of ~3-4 mm in diameter, animals from appropriate groups were injected with vaccine (E7-100 μg/mouse, PADRE-20 μg/mouse, QuilA-10 μg/mouse) s.c. Mice from proper groups were supplied with 1-MT in drinking water (2 mg/ml) also starting day 10 after tumor implantation throughout the experiment. Mice were treated with vaccine weekly throughout the experiment; anti-OX40 antibody was given twice a week. Tumors were measured every 3-4 days using digital calipers, and tumor volume was calculated using the formula $V=(W^2 \times L)/2$, whereby V is volume, L is length (longer diameter), and W is width (shorter diameter). In these experiments, mice were sacrificed when they became moribund, tumors were ulcerated, or tumor volume reached 1.5 cm³.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for enhancing an immune response against a tumor antigen in a subject, the method comprising administering to the subject an OX40 agonist antibody or an antigen-binding fragment thereof, 1-methyltryptophan (1-MT), and an immunogenic composition comprising an HPV antigen, thereby enhancing the subject's immune response against the tumor antigen relative to administration of the immunogenic composition and the OX40 agonist antibody or an antigen-binding fragment thereof.

2. A method for delaying or reducing tumor growth in a subject, the method comprising administering to the subject an OX40 agonist antibody or an antigen-binding fragment thereof, 1-methyltryptophan (1-MT) and an immunogenic composition comprising an HPV antigen, thereby delaying or reducing tumor growth in the subject relative to administration of the immunogenic composition and the OX40 agonist antibody or an antigen-binding fragment thereof.

3. The method of either of claim 1 or 2, wherein the subject has an HPV-associated cancer.

* * * * *

SEQUENCE LISTING

<160> NUMBER OF SEQ ID NOS: 1

<210> SEQ ID NO 1
<211> LENGTH: 270

```
<212> TYPE: PRT
<213> ORGANISM: Homo sapiens

<400> SEQUENCE: 1

Met Cys Val Gly Ala Arg Arg Gly Arg Gly Pro Cys Ala Ala Gly Gly
1               5                   10                  15

Ser Thr Val Thr Gly Leu His Cys Val Gly Asp Thr Tyr Pro Ser Asn
                20                  25                  30

Asp Arg Cys Cys His Glu Cys Arg Pro Gly Asn Gly Met Val Ser Arg
            35                  40                  45

Cys Ser Arg Ser Gln Asn Thr Val Cys Arg Pro Cys Gly Pro Gly Phe
        50                  55                  60

Tyr Asn Asp Val Val Ser Ser Lys Pro Cys Lys Pro Cys Thr Trp Cys
65                  70                  75                  80

Asn Leu Arg Ser Gly Ser Glu Arg Lys Gln Leu Cys Thr Ala Thr Gln
                85                  90                  95

Asp Thr Val Cys Arg Cys Arg Ala Gly Thr Gln Pro Leu Asp Ser Tyr
                100                 105                 110

Lys Pro Gly Val Asp Cys Ala Pro Cys Pro Pro Gly His Phe Ser Pro
            115                 120                 125

Gly Asp Asn Gln Ala Cys Lys Pro Trp Thr Asn Cys Thr Leu Ala Gly
        130                 135                 140

Lys His Thr Leu Gln Pro Ala Ser Asn Ser Ser Asp Ala Ile Cys Glu
145                 150                 155                 160

Asp Arg Asp Pro Pro Ala Thr Gln Pro Gln Glu Thr Gln Gly Pro Pro
                165                 170                 175

Ala Arg Pro Ile Thr Val Gln Pro Thr Glu Ala Trp Pro Arg Thr Ser
                180                 185                 190

Gln Gly Pro Ser Thr Arg Pro Val Glu Val Pro Gly Gly Arg Ala Val
            195                 200                 205

Ala Ala Ile Leu Gly Leu Gly Leu Val Leu Gly Leu Leu Gly Pro Leu
            210                 215                 220

Ala Ile Leu Leu Ala Leu Tyr Leu Leu Arg Arg Asp Gln Arg Leu Pro
225                 230                 235                 240

Pro Asp Ala His Lys Pro Pro Gly Gly Gly Ser Phe Arg Thr Pro Ile
                245                 250                 255

Gln Glu Glu Gln Ala Asp Ala His Ser Thr Leu Ala Lys Ile
                260                 265                 270
```